United States Patent
Urano et al.

(10) Patent No.: US 9,506,102 B2
(45) Date of Patent: Nov. 29, 2016

(54) FLUORESCENT PROBE FOR HIGH-SENSITIVITY PANCREATIC FLUID DETECTION, AND METHOD FOR DETECTING PANCREATIC FLUID

(71) Applicant: THE UNIVERSITY OF TOKYO, Tokyo (JP)

(72) Inventors: Yasuteru Urano, Tokyo (JP); Masayo Sakabe, Tokyo (JP); Tetsuo Nagano, Tokyo (JP); Takeaki Ishizawa, Tokyo (JP); Suguru Yamashita, Tokyo (JP); Norihiro Kokudo, Tokyo (JP); Mako Kamiya, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 66 days.

(21) Appl. No.: 14/398,202

(22) PCT Filed: May 29, 2013

(86) PCT No.: PCT/JP2013/064921
§ 371 (c)(1),
(2) Date: Feb. 13, 2015

(87) PCT Pub. No.: WO2013/180181
PCT Pub. Date: Dec. 5, 2013

(65) Prior Publication Data
US 2015/0152469 A1   Jun. 4, 2015

(30) Foreign Application Priority Data

May 30, 2012 (JP) ................................. 2012-123478

(51) Int. Cl.
C12Q 1/37 (2006.01)
C12Q 1/48 (2006.01)
C09B 11/24 (2006.01)
C07D 493/10 (2006.01)
C09K 11/06 (2006.01)

(52) U.S. Cl.
CPC .............. *C12Q 1/37* (2013.01); *C07D 493/10* (2013.01); *C09B 11/24* (2013.01); *C09K 11/06* (2013.01); *C12Q 1/48* (2013.01); *C09K 2211/1007* (2013.01); *C09K 2211/1011* (2013.01); *C09K 2211/1088* (2013.01)

(58) Field of Classification Search
None
See application file for complete search history.

(56) References Cited

U.S. PATENT DOCUMENTS

2012/0052518 A1   3/2012   Nagano et al.

FOREIGN PATENT DOCUMENTS

| EP | 2399920 A1 | 12/2011 |
| EP | 2524702 A1 | 11/2012 |
| WO | 2010-095450 A1 | 8/2010 |
| WO | 2011/087000 A1 | 7/2011 |

OTHER PUBLICATIONS

Hao et al., "DD&T Drug Discoveries & Therapeutics", www.Ddtjournal.com; vol. 6, Oct. 2012.
Drano, Yasuteru et al., "Rapid Cancer Detection by Topically Spraying a γ-Glutamyltranspeptidase-Activated Fluorescent Prove", www.ScienceTranslationalMedicine.org; vol. 3, Issue 107-111, Nov. 23, 2011, pp. 152-161.
O. Facy et al., "Diagnosis of postoperative pancreatic fistula", British Journal of Surgery; vol. 99, No. 8, Apr. 27, 2012, pp. 1072-1075.
Extended European Search Report issued in Patent Application No. 13797296.4, dated Oct. 5, 2015.
D. Fuks et al., "Life-threatening postoperative pancreatic fistula (garde C) after pancreaticoduodenectomy: incidence, prognosis, and risk factors", The American Journal of Surgery, vol. 197, 2009, pp. 702-709.
C. Bassi et al., "Postoperative pancreatic fistula: An international study group (ISGPF) definition", Surgery, vol. 138, 2005, pp. 8-13.

(Continued)

*Primary Examiner* — Noble Jarrell
(74) *Attorney, Agent, or Firm* — Greenblum and Bernstein, P.L.C.

(57) ABSTRACT

A fluorescent probe for detecting pancreatic fluid containing a compound or salt thereof represented by formula (I) below.

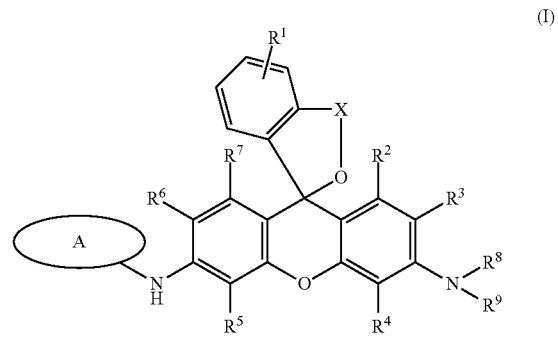

(In the formula, A represents an amino acid residue or N-substituted amino acid residue, with A forming an amide bond with the adjacent NH in the formula; $R^1$ represents a hydrogen atom or 1 to 4 same or different substituent groups that bond with a benzene ring; $R^2$, $R^3$, $R^4$, $R^5$, $R^6$, and $R^7$ each independently represent a hydrogen atom, a hydroxyl group, an alkyl group, or a halogen atom; $R^8$ and $R^9$ each independently represent a hydrogen atom or an alkyl group; and X represents a $C^1$-$C^3$ alkylene group).

15 Claims, 6 Drawing Sheets

(56) References Cited

OTHER PUBLICATIONS

E. Molinari et al., "Amylase value in drains after pancreatic resection as predictive factor of postoperative pancreatic fistula" Annals of surgery, vol. 246 No. 2, 2007, pp. 281-287.
H. Shinchi et al., "The usefulness of drain data to identify a clinically relevant pancreatic anastromotic leak after pancreaticoduodenectomy?", Journal of gastrointestinal surgery, vol. 10, 2006, pp. 490-498.
YM. Shyr et al., "Does drainage fluid amylase reflect pancreatic leakage after pancreaticoduodenectomy?" World J. Surg, vol. 27, 2003, pp. 606-610.
Takeaki Ishizawa, "Keiko Navigation o Oyo shita Kyoshika Kantansui Shujutsu no Kaihatsu", Japanese Society of Hepato-Biliary-Pancreatic Surgery. Gakujutsu Shukai Program Shorokushu, vol. 24, May 23, 2012, pp. 201.
International Search Report from Application No. PCT/JP2013/064921, mail date is Sep. 3, 2013.

(a)

(b)

(a)

gPhe-HMRG : 50 μM
Trp : 26.3 BTEEmunits/mL
A spray was used.
The blood was not adhered thereto.
Adhesion of the pancreatic duct and
 the pancreatic juice was confirmed within the red line.

(b)

(a)

(b)

FLUORESCENT PROBE FOR HIGH-SENSITIVITY PANCREATIC FLUID DETECTION, AND METHOD FOR DETECTING PANCREATIC FLUID

TECHNICAL FIELD

The present invention relates to a fluorescent probe for pancreatic fluid detection. More particularly, the invention relates to a fluorescent probe for detecting a protease activity in a pancreatic fluid, a detection method using the fluorescent probe, and a detection kit including the probe.

BACKGROUND ART

The death toll from pancreatic cancer goes on increasing year by year, and is ranked high in the worldwide cause-specific statistics of cancer death. However, there are very few effective treatment methods for pancreatic cancer, and, as an almost only treatment method for which a complete cure can be expected, surgical excision of a cancerous part has been conducted. In addition, also for bile duct cancer, when cancer development or metastasis is recognized at the junction with the pancreas, simultaneous excision of the pancreas is selected.

At the moment, the number of such surgeries of pancreas excision reaches about 40,000 in the United States, and also, 10,000 or more in Japan. However, it has been reported that a mortality rate after surgeries reaches several percent even in an experienced medical facility, and that the mortality rate is further increased in cases of medical doctors less-experienced in surgeries. As one of the causes, "pancreatic fluid leakage" in which the pancreatic fluid leaks from a pancreas section after pancreas excision can be mentioned. When the pancreatic fluid leakage occurs, there is a risk that not only bacterial infections are caused, but also blood vessels are digested by a self-digestion action of the pancreatic fluid, causing serious bleeding and thus resulting in death (NPL 1). Therefore, pancreatic fluid leakage has been the most important issue in pancreatectomies. Although various pancreatectomy techniques and postoperative management techniques have been studied in order to prevent occurrence of pancreatic fluid leakage and its intensification, pancreatic fluid leakage still occurs at a frequency of 30% to 50%.

Factors that make it difficult to prevent pancreatic fluid leakage are as follows: not only is it difficult to carry out a ligature treatment to all stumps of pancreatic ducts because normal pancreatic ducts are very thin, and therefore, are difficult to identify, but also there is no technique which can visualize leakage of colorless and transparent pancreatic fluid during surgeries. At the moment, measurement on a concentration of amylase, which is a glycolytic enzyme in an intraperitoneal drainage fluid, the measurement proposed by ISGPF (International study group on pancreatic fistula), has been used as a technique for detecting pancreatic fluid leakage (NPLs 2 and 3). However, this technique not only requires time until acquisition of detection results, but also does not directly measure a protease, which is considered to act a major role in the above-described self-digestion action of the pancreatic fluid, causing serious complications after surgeries, and therefore, it has been pointed out that the technique does not always accurately reflect seriousness of the pancreatic fluid leakage after surgeries (NPLs 4 and 5).

Because of such circumstances, it has been strongly desired to establish a novel method of detecting pancreatic fluid leakage for identifying pancreatic ducts and for quickly and appropriately confirming leakage of pancreatic fluid during surgeries, as an alternative to the conventional method by the measurement of an amylase concentration.

CITATION LIST

Non Patent Literature

NPL 1: D. Fuks et al., Am J Surg., 2009, 197, 702-709.
NPL 2: C. Bassi et al., Surgery., 2005, 138, 8-13.
NPL3: E. Molinari, C. Bassi, R. Salvia, et al., Ann Surg., 2007, 246, 281-287.
NPL 4: H. Shinchi, K. Wada, L W. Traverso, J Gastrointest Surg., 2006, 10, 490-498.
NPL 5: Y M. Shyr, C H. Su, C W. Wu, et al., World J Surg., 2003, 27, 606-610

DISCLOSURE OF INVENTION

Technical Problem

A problem to be solved by the invention is to provide a fluorescent probe which allows quick and high-sensitive detection and imaging of the presence of leakage of a pancreatic fluid during or after surgeries, and moreover to provide a detection method and a detection kit using the fluorescent probe.

Solution to Problem

The present inventors conducted intensive studies to solve the above problem. Consequently, the present inventors found that the presence or absence of chymotrypsin or the like, which is a protease included in pancreatic fluid, can specifically be detected as an on/off fluorescent response by using, as a fluorescent probe, a compound of a xanthene skeleton having an amino acid residue, and that this allows quick and high-sensitive detection of a pancreatic fluid. Furthermore, the present inventors found that, by simple procedures where excised surface of the pancreas immediately after being excised by surgeries is adhered to a slip of paper or the like, and the above-mentioned fluorescent probe is sprayed onto the slip of paper or the like, imaging of a pancreatic fluid becomes possible only 1 minute after spraying the probe, thereby it is possible to detect and locate the pancreatic fluid leakage in a very easy manner. Based on these findings, the present inventors finally completed the invention.

That is, in one aspect, the invention provides a fluorescent probe for pancreatic fluid detection, including a compound represented by the following formula (I) or a salt thereof:

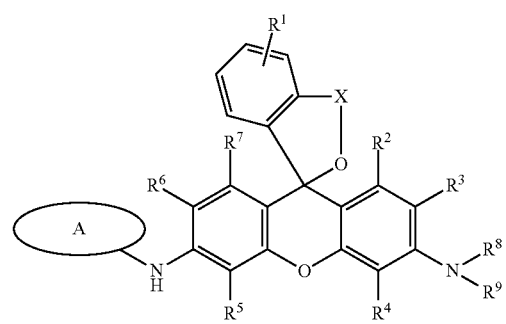

wherein A represents an amino acid residue or an N-substituted amino acid residue, where A forms an amide bond with the adjacent NH in the formula, thus linking to the NH; $R^1$ represents a hydrogen atom, or one substituent group or two to four substituent groups which are identical to or different from each other binding to the benzene ring; $R^2$, $R^3$, $R^4$, $R^5$, $R^6$ and $R^7$ each independently represent a hydrogen atom, a hydroxy group, an alkyl group or a halogen atom; $R^8$ and $R^9$ each independently represent a hydrogen atom or an alkyl group; and X represents a $C_1$-$C_3$ alkylene group. Preferably, $R^1$, $R^2$, $R^3$, $R^4$, $R^5$, $R^6$, $R^7$, $R^8$ and $R^9$ are hydrogen atoms, and X is a methylene group.

An amino acid constituting the above amino acid residue and N-substituted amino acid residue representing A is selected preferably from hydrophobic amino acids, more preferably from aromatic amino acids. These are particularly favorable when the fluorescent probe of the invention targets chymotrypsin.

In a preferred embodiment of the invention, A is a group represented by the following formula (II). Here, the carbonyl group in the formula (II) and the NH in the formula (I) link to each other by forming an amide bond.

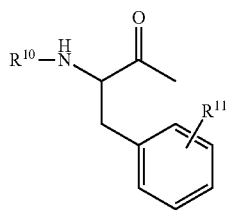

(II)

In the formula, $R^{10}$ is a substituted or unsubstituted acyl group. The substituted acyl group may be an amino acid residue in which a hydroxy group is removed from the carboxy group, or a group resulted from removal of a hydroxy group from the C-terminal carboxy group of a peptide chain containing of 1 to 5 amino acids. The substituent group can have one substituent group or more than two substituent groups which are identical to or different from each other. $R^{10}$ is preferably selected from among an acetyl group, a carbobenzoxy group, a benzoyl group, a succinyl group, a glutaryl group, or a substituent group containing them as one part. When $R^{10}$ is an amino acid residue in which a hydroxy group is removed from the carboxy group, or a group resulted from removal of a hydroxy group from the C-terminal carboxy group of a peptide chain containing of 1 to 5 amino acids, the N-terminus of either one is preferably substituted with an acetyl group, a carbobenzoxy group, a benzoyl group, a succinyl group, glutaryl group, or a substituent group containing them as one part. Additionally, $R^{11}$ represents a hydrogen atom or a hydroxy group, and, when $R^{11}$ is a hydroxy group, $R^{11}$ is preferably located at the para position.

In one preferable aspect of the invention, A is one substituent group selected from groups represented by the following formulas (III) to (VI). Here, the carbonyl group in the phenylalanine residue moiety in the formula (III) and the NH in the formula (I) link to each other by forming an amide bond. The same applies to formulas (V) to (VI). Additionally, the carbonyl group in the tyrosine residue moiety in the formula (IV) and the NH in the formula (I) link to each other by forming an amide bond.

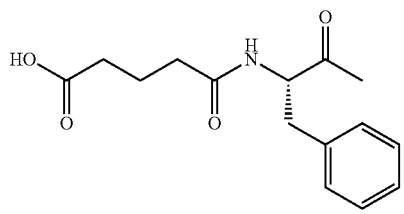

(III)

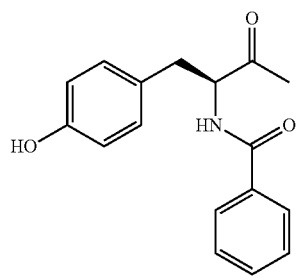

(IV)

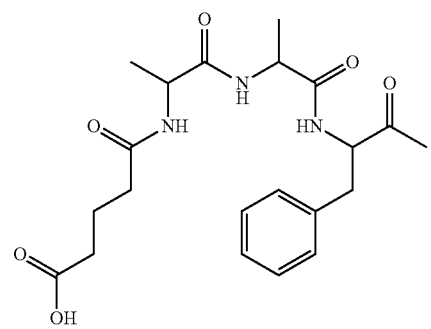

(V)

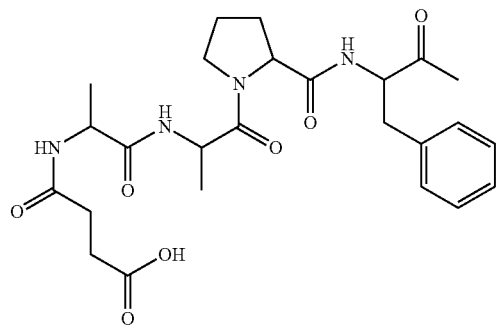

(VI)

Furthermore, when the fluorescent probe of the invention targets γ-glutamyltransferase, an aspect in which A is a γ-glutamyl group is favorable.

In another aspect, the invention provides a method for detecting pancreatic fluid, comprising: contacting the above-described fluorescent probe with a body fluid sample; and observing a fluorescence response or absorbance change caused by a reaction of a protease included in the sample and the fluorescent probe to thereby detect a presence of a pancreatic fluid.

In a preferable aspect, the above protease is chymotrypsin or γ-glutamyltransferase, and is more preferably chymotrypsin.

When the above protease is chymotrypsin, trypsin is preferably added to the body fluid sample in contacting the fluorescent probe with the body fluid sample. This is because chymotrypsin is secreted as chymotrypsinogen, which is a precursor, into the pancreatic fluid, and therefore, chymotrypsinogen is favorably converted to the activated form, chymotrypsin, by addition of trypsin, followed by the measurement based on the fluorescent probe of the invention.

Preferably, in the detection method of the invention, the fluorescence response can be visualized by a fluorescent imaging method. When parts suspected of pancreatic fluid leakage are adhered to a slip of paper or the like, and the fluorescent probe is sprayed thereto, the fluorescent response by the probe molecule can be displayed bidimensionally by use of a fluorescent imaging method. Therefore, position of pancreatic ducts and parts where pancreatic fluid leakage occurs can instantly and visually be recognized.

In still another aspect, the invention provides a kit for pancreatic fluid detection, including: the above-described fluorescent probe. When the above protease is chymotrypsin, the kit is preferably a kit for pancreatic fluid detection, including: the above-described fluorescent probe, and trypsin; wherein the fluorescent probe and the trypsin are stored such that the fluorescent probe and the trypsin are not mixed until the kit is used.

Advantageous Effects of Invention

The invention brings about excellent effects in which, by using the compound of a xanthene skeleton having an amino acid residue as a fluorescent probe, chymotrypsin or the like, which is a protease included in the pancreatic fluid, can specifically be detected as an on/off fluorescent response in a short time, thereby allowing quick and high-sensitive detection and imaging of the presence of leakage of the pancreatic fluid during or after surgeries.

According to the fluorescent probe and the detection method of the invention, detection of the pancreatic fluid is possible in only several minutes by only carrying out simple manipulation where the fluorescent probe is added to a specimen, and, additionally, a protease activity, which is a major cause of complications after surgeries due to pancreatic fluid leakage, can directly be measured. Therefore, the fluorescent probe and the detection method are excellent in respect that the pancreatic fluid can more quickly be detected with higher reliability, compared with the conventional detection of pancreatic fluid based on measurement on an amylase concentration.

Moreover, according to the invention, since positions of pancreatic ducts and pancreatic fluid leakage caused from discussion of the pancreas can accurately be identified with a fluorescent imaging measure, leakage sites of the pancreatic fluid can certainly be closed by additional saturation or the like, thereby preventing occurrence of pancreatic fluid leakage, and therefore, prevention of serious complications due to pancreatic fluid leakage becomes possible.

Furthermore, when the presence or absence of leakage of the pancreatic fluid from stumps of the pancreas was confirmed by the invention during surgeries, occurrence of the pancreatic leakage was significantly higher in cases where fluorescent responses were recognized, than in cases where fluorescent responses were not recognized. Therefore, it becomes possible to distinguish a group at high risk of pancreatic fluid leakage after surgeries and to more safely and efficiently carry out drain management after surgeries than ever before, and thus, the invention contributes to improvements in occurrence of serious pancreatic fluid leakage and the resulting hospital mortality.

As described above, not only detection procedures of the invention are simple, but also the invention can be carried out with visible light which is safe to the living body, and the quantity of the fluorescent probe used therein is also very minute. Therefore, visualization of pancreatic fluid leakage by direct spraying of the fluorescent probe into the living body is also fully possible, and thus, in these points, the invention is practically excellent.

Accordingly, by using the invention during surgical abdominal operations or laparoscopic surgeries, protease activities in pancreatic fluid of individual subjects can quickly be recognized, and therefore, the invention is also beneficial in selection of an operative method.

BRIEF DESCRIPTION OF DRAWINGS

FIG. 7a is a white light image for showing adhesion positions of pancreatic fluid. The left side of FIG. 7b indicates color images at 500-720 nm, and the right side thereof indicates fluorescent images at 540 nm.

FIG. 8a is a white light image for showing adhesion positions of pancreatic fluid. The left side of FIG. 8b indicates color images at 500-720 nm, and the right side thereof indicates fluorescent images at 540 nm.

DESCRIPTION OF EMBODIMENTS

Figure 1:
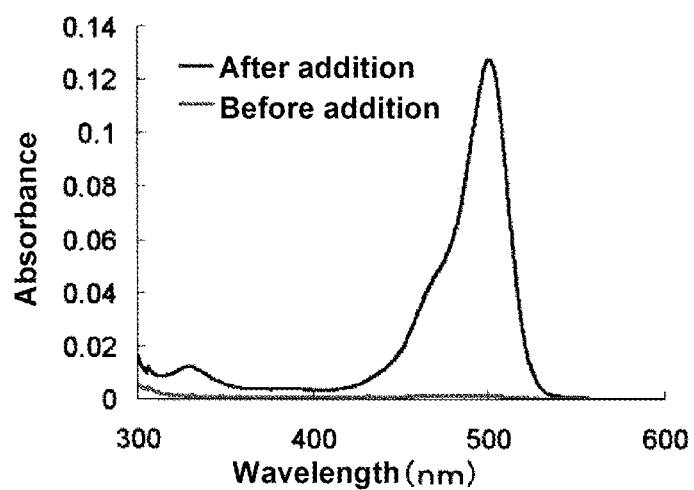
FIG. 1 is a diagram showing absorption spectral changes (FIG. 1a) and fluorescent spectral changes (FIG. 1b) by chymotrypsin addition to gPhe-HMRG which is a fluorescent probe of the invention.
Figure 1:
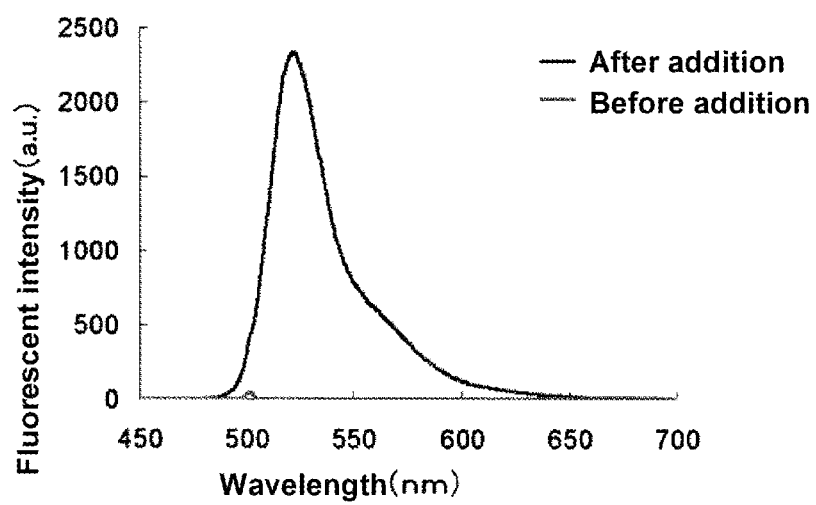

Hereinafter, embodiments of the invention will be described. The scope of the invention is not limited to the descriptions, and the invention can be carried out with proper modifications without impairing the essence of the invention.

In the specification, an alkyl group may be either of a linear alkyl group, a branched-chain alkyl group, a cyclic alkyl group, or an alkyl group containing of their combinations. Although the carbon number of the alkyl group is not particularly limited, for example, the carbon number is about 1 to 6, preferably about 1 to 4. In the specification, the alkyl group may have one or more optional substituent groups. For example, the substituent groups include an alkoxy group, a halogen atom (which may be any of a fluorine atom, a chlorine atom, a bromine atom or an iodine atom), an amino group, a mono or di-substituted amino group, a substituted silyl group, an acyl group, or the like. However, the substituent groups are not limited to these examples. When the alkyl groups has two or more substituent groups, they may be identical to or different from each other. The same applies to alkyl moieties of other substituent groups including alkyl moieties (e.g. an alkyloxy group, an aralkyl group, etc.).

Additionally, in the specification, an aryl group may be either of a monocyclic aryl group or a condensed polycyclic aryl group, and may include one or more heteroatoms (e.g., an oxygen atom, nitrogen atom, sulfur atom, etc.) as ring-constituting atoms. In the specification, the aryl group may have one or more optional substituent groups on the ring. For example, the substituent groups include an alkoxy group, a halogen atom, an amino group, a mono- or di-substituted amino group, a substituted silyl group, an acyl group, or the like. However, the substituent groups are not limited to these examples. When the aryl group has two or more substituent groups, they may be identical to or different from each other. The same applies to aryl moieties of other substituent groups including aryl moieties (e.g., an aryloxy group, an aralkyl group, etc.).

(1) Fluorescent Probe Molecule

In one aspect, the fluorescent probe of the invention is a compound having a structure represented by the following general formula (I).

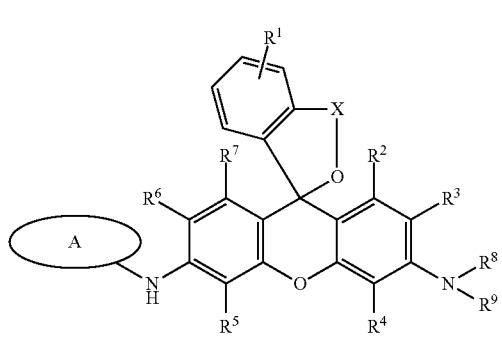

(I)

In the above general formula (I), $R^1$ represents a hydrogen atom or 1 to 4 substituent groups which bind to the benzene ring. For example, the substituent groups include an alkyl group, an alkoxy group, a halogen atom, an amino group, a mono or di-substituted amino group, a substituted silyl group, an acyl group, or the like. However, the substituent groups are not limited to these examples. When the compound has two or more substituent groups on the benzene ring, they may be identical to or different from each other. For $R^1$, a hydrogen atom is preferable.

$R^2$, $R^3$, $R^4$, $R^5$, $R^6$ and $R^7$ each independently represent a hydrogen atom, a hydroxy group, an alkyl group or a halogen atom. It is preferable that $R^2$ and $R^7$ are hydrogen atoms. Additionally, it is also preferable that $R^3$, $R^4$, $R^5$ and $R^6$ are hydrogen atoms. It is more preferable that all of $R^2$, $R^3$, $R^4$, $R^5$, $R^6$ and $R^7$ are hydrogen atoms.

$R^8$ and $R^9$ each independently represent a hydrogen atom or an alkyl group. When both $R^8$ and $R^9$ represent an alkyl group, they may be identical to or different from each other. For example, a case where both $R^8$ and $R^9$ are hydrogen atoms, and a case where $R^8$ is an alkyl group and $R^9$ is a hydrogen atom are preferable. A case where both $R^8$ and $R^9$ are hydrogen atoms is more desirable.

X represents a $C^1$-$C^3$ alkylene group. The alkylene group may be either of a linear alkylene group or a branched-chain alkylene group. For example, a methylene group (—$CH_2$—), an ethylene group (—$CH_2$—$CH_2$—), and a propylene group (—$CH_2$—$CH_2$—$CH_2$—), as well as branched-chain alkylene groups such as —$CH(CH_3)$—, —$CH_2$—$CH(CH_3)$—, and —$CH(CH_2CH_3)$— can be sued. Among them, a methylene group or an ethylene group is preferable, and a methylene group is more preferable.

A represents an amino acid residue or an N-substituted amino acid residue. In the specification, the "amino acid residue" is equivalent to a remaining partial structure resulted from removal of a hydroxy group from a carboxy group of an amino acid, and means that having the same structure as that of a so-called N-terminal residue. However, this does not exclude a case where A is formed by joining of plural amino acid residues. In that case, the amino acid residue at the C-terminus may have a partial structure resulted from removal of a hydroxy group from a carboxy group of an amino acid, as described above, and removal of a hydrogen atom from the amino group, and intermediate and N-terminal amino acid residues can be joined in the same manner as general peptide chains.

Therefore, A links to the adjacent NH in the formula by forming an amide bond. That is, the carbonyl moiety of the amino acid residue and the NH in the formula (I) form an amide bond, and thus, A links to the xanthene skeleton. In addition, the "N-substituted amino acid residue" refers to an amino acid residue resulted from substitution of a hydrogen atom in the amino group of the above-described amino acid residue.

In the specification, for the "amino acid", any compound can be used as long as the compound has both an amino group and a carboxy group, and the amino acid includes natural and unnatural compounds. The amino acid may be either of a neutral amino acid, a basic amino acid, or an acidic amino acid, and, besides amino acids which function as transmitters, such as neurotransmitters, by themselves, amino acids which are components of polypeptide compounds such as physiologically active peptides (including dipeptides, tripeptides, tetrapeptides, as well as oligopeptides) or proteins can be used. For example, the amino acid may be an α-amino acid, a β-amino acid, a γ-amino acid or the like. For the amino acid, an optically-active amino acid is preferably used. For example, although either of a D- or L-amino acid may be used for the α-amino acid, there are cases where an optically-active amino acid which functions in the living body is preferably selected.

Here, in terms of specific detection of a certain protease, for A, an amino acid residue which allows cleavage of the amide bond A-NH in the formula (I) due to hydrolysis by a target protease is preferably used. Nonlimitative examples of such an amino acid include 20 types of L-amino acids which constitute proteins, as well as selenocysteine, pyrrolysine, cystine, hydroxyproline, hydroxylysine, thyroxine, O-phosphoserine or desmosine, and β-alanine, sarcosine, ornithine, creatine, γ-aminobutyric acid, opine, and the like.

For example, when chymotrypsin included in pancreatic fluid is targeted for fluorescence detection, the amino acid residue in A is preferably constituted of an aromatic amino acid or hydrophobic amino acid. Nonlimitative examples of such an amino acid include phenylalanine, tryptophan, tyrosine, leucine, isoleucine, norleucine, valine, norvaline, methionine and their N-substituted residues. However, phenylalanine, tryptophan, tyrosine and their N-substituted residues are preferable, and phenylalanine and an N-substituted phenylalanine residue, tyrosine as well as N-substituted tyrosine are more preferable.

In addition, when γ-glutamyltransferase included in pancreatic fluid is targeted for fluorescence detection, A is favorably γ-glutamyl.

Preferable embodiments of A are an N-substituted phenylalanine residue and an N-substituted tyrosine residue represented by the following formula (II), and these are preferable when chymotrypsin is targeted as described above.

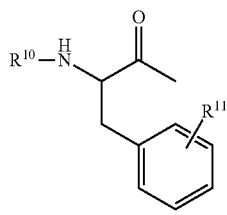
(II)

The carbonyl group in the formula (II) and the NH in the formula (I) form an amide bond, and thus, the formula (II) links to the xanthene skeleton of the formula (I).

$R^{10}$ is a substituted or unsubstituted acyl group. Here, the acyl group may include one or two or more heteroatoms, and may also have one or more optional substituent groups. For example, the substituent groups include an alkyl group, an alkenyl group, an alkynyl group, an aryl group, an alkoxy group, an amide group, a halogen atom, an amino group, a mono- or di-substituted amino group, a substituted silyl group, an acyl group, or the like. However, the substituent groups are not limited to these examples. When the acyl group has two or more substituent groups, they may be identical to or different from each other. The substituted acyl group may be an amino acid residue resulted from removal of a hydroxy group from a carboxy group. More preferably, $R^{10}$ is an aliphatic acyl group or an aromatic acyl group, and may also be an aliphatic acyl group having an aromatic group as a substituent group. These substituent groups may also include one or two or more heteroatoms, and may further have one or more optional substituent groups in the same manner as described above. Furthermore, $R^{10}$ is preferably an acyl group having, at a terminus of $R^{10}$, a polar group such as a carboxy group, an amino group, a carbonyl group, an amide group or a hydroxy group. In one embodiment, $R^{10}$ is preferably an acetyl group ($CH_3CO$—), a carbobenzoxy group (cbz group) ($C_6H_5CH_2OCO$—), a benzoyl group ($C_6H_5CO$—), a succinyl group (HOOC—$CH_2CH_2CO$—), a glutaryl group (HOOC—$CH_2CH_2CH_2CO$—) or a substituent group including them as one part. When $R^{10}$ is an amino acid residue resulted from removal of a hydroxy group from the carboxy group, or a group resulted from removal of a hydroxy group from a C-terminal carboxy group of a peptide chain consisting of 1 to 5 amino acids, the N-terminus, namely the N-terminus of the amino acid residues, in either case is preferably a group selected from among an acetyl group, a carbobenzoxy group, a benzoyl group, a succinyl group, a glutaryl group or a substituent group including them as one part. In addition, $R^{11}$ represents a hydrogen atom or hydroxy group, and, when $R^{11}$ is a hydroxy group, $R^{11}$ is preferably located at the para position.

One preferable embodiment of A is one substituent group selected from groups represented by the following formulas (III) to (VI). These are preferable when chymotrypsin is targeted as described above.

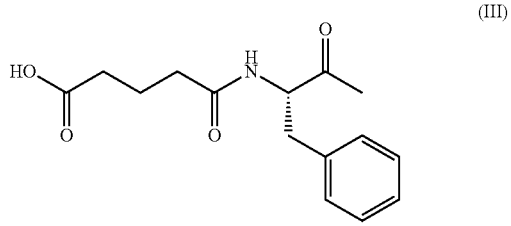
(III)

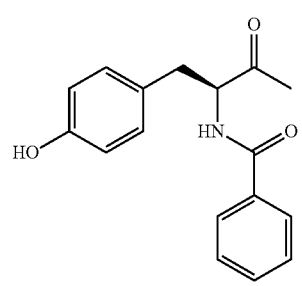
(IV)

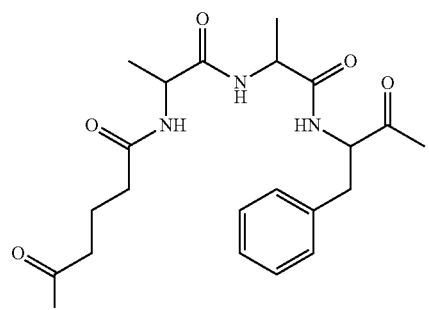
(V)

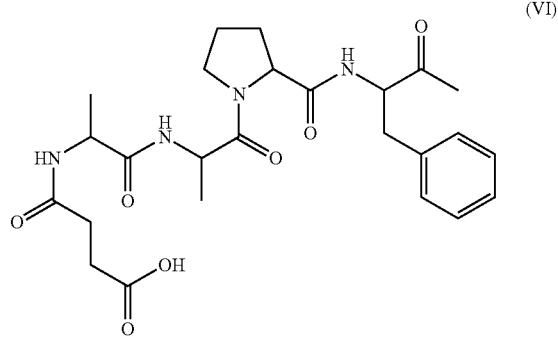
(VI)

There are cases where the compound represented by the above general formula (I) (including cases where A adopts embodiments of formulas (II) to (VI), and the same applies to the descriptions below) exists as a salt. Such a salt includes a base addition salt, an acid addition salt, an amino acid salt, and the like. For example, the base addition salt includes metal salts such as a sodium salt, a potassium salt, a calcium salt and a magnesium salt; ammonium salts; or organic amine salts such as triethylamine salts, piperidine salts and morpholine salts. The acid addition salt includes, for example, mineral acid salts such as hydrochlorides, sulfates and nitrates; and organic acid salts such as methanesulfonates, p-toluenesulfonates, citrates and oxalates. The amino acid salt includes, for example, glycine salts and the like. However, salts of the compound of the invention are not limited to these examples.

There are cases where the compound represented by the general formula (I) has one or two or more asymmetric carbons, depending on a type of the substituent group, and there are cases where stereoisomers such as optical isomers or diastereoisomers exist. Any of stereoisomers of pure forms, any mixtures of stereoisomers, racemic bodies and the like are all encompassed within the scope of the invention.

There are cases where the compound represented by the general formula (I) or salt thereof exists as a hydrate or solvate, and both of these substances are encompassed within the scope of the invention. A type of a solvent forming such a solvate is not particularly limited. However, solvents such as ethanol, acetone and isopropanol can be mentioned as examples thereof.

For example, the compound represented by the general formula (I) can easily be produced as follows: a xanthene compound or the like having amino groups at the positions 3 and 6 and having a 2-carboxyphenyl group or a 2-alkoxycarbonylphenyl group at the position 9 is used as a raw material, the 2-carboxyphenyl group or the 2-alkoxycarbonylphenyl group at the position 9 is converted to a hydroxyalkyl group, and then, an amino acid residue or an N-substituted amino acid residue is bound to the amino group at the position 3. As examples of 3,6-diaminoxanthene compounds which are usable as raw materials, rhodamine 110, rhodamine 123 and the like which are all commercially-available, can be mentioned. However, the raw material is not limited to these compounds, and an appropriate xanthene compound can be selected depending on a structure of an objective compound. In addition, by using a compound having a skeleton according to an embodiment in which the oxygen atom in the xanthene skeleton moiety of the compound represented by the general formula (I) is substituted with a carbon atom or silicon atom having a specific substituent group, germanium atom, tin atom or lead atom, a fluorescent probe having the same function as the general formula (I) in the invention can also be produced.

In Examples of the specification, production methods are specifically shown with respect to typical compounds encompassed by the compound of the invention represented by the general formula (I). Therefore, one skilled in the art can easily produce any compounds encompassed by the general formula (I) by referring to the disclosure of the specification and by properly selecting a starting material or reagents, reaction conditions, etc., as needed.

(2) Light Emission Mechanism of Fluorescent Probe Molecules

The fluorescent probe of the invention itself is substantially nonfluorescent in a neutral region (e.g. a range of pH 5-9) in a state where the upper part of the xanthene skeleton represented by the general formula (I) is closed. On the other hand, when the amide bond with A-NH is hydrolyzed by a protease, the compound immediately turned into a ring-opened tautomer, and the following compound exhibiting strong fluorescence is generated.

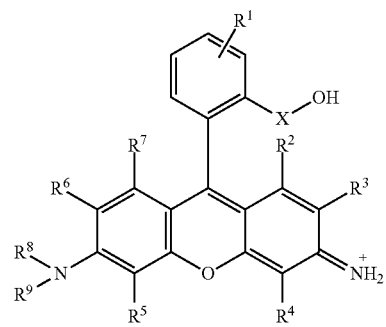

In other words, the fluorescent probe of the invention, including the compound represented by the general formula (I) or salt thereof as an active ingredient, have properties that the compound or salt is hydrolyzed by a protease present in the pancreatic fluid, thereby providing the above-described ring-opened compound emitting strong fluorescence, and therefore, emits strong fluorescence in several tens of seconds to several minutes by addition of the fluorescent probe to specimens such as body fluids. Accordingly, by using the fluorescent probe of the invention, the protease activity is measured based on changes in fluorescent intensities, and the presence of pancreatic fluid including a protease can be detected.

More particularly, for example, the compound represented by the general formula (I) or salt thereof scarcely emits fluorescence in a neutral region, for example, when irradiated with excitation light of about 440-500 nm. However, the above-described ring-opened compound has a property of emitting very strong fluorescence (e.g. emission: 524 nm) under the same conditions. Therefore, when detection is carried out with the fluorescent probe of the invention, generally, visible light of about 440-500 nm, preferably about 445-490 nm, more preferably visible light of about 450-480 nm may be used for irradiation. The fluorescence wavelength to be observed is generally about 510-800 nm, and, for example, fluorescence of about 516-556 nm is preferably observed.

(3) Pancreatic Fluid Detection Method Using the Fluorescent Probe.

In the pancreatic fluid detection method of the invention, the above-described fluorescent probe is contacted with a body fluid sample, and a fluorescence response caused by a reaction of a protease included in the sample and the fluorescent probe is observed, thereby detecting the presence of a pancreatic fluid. In a preferable embodiment, the protease is chymotrypsin or γ-glutamyltransferase, and, is more preferably chymotrypsin. In the specification, the term "detection (or detect(s), detecting or detected)" should be interpreted in the broadest meaning including measurements of various purposes such as quantitative or qualitative measurements. In addition, the compound represented by the general formula (I) or salt thereof hardly absorbs light of a wavelength of 350 nm or more in a neutral region. However, when the compound or salt thereof converts to the above-mentioned ring-opened compound due to hydrolysis by a protease present in the pancreatic fluid, the absorption spectrum in the ultraviolet-visible region varies with its structural changes, and the ring-opened compound absorbs light of a wavelength of 350 nm or more. Therefore, in some cases, the reaction of the protease and the fluorescent probe can also be detected based on changes in the ultraviolet-visible absorption spectrum (e.g. changes of absorbance at a specific absorption wavelength).

Chymotrypsin is secreted as chymotrypsinogen, which is a precursor, into pancreatic fluid, and it has been known that chymotrypsinogen is activated by a reaction with trypsin. Therefore, after chymotrypsinogen is converted to the activated form chymotrypsin by addition of trypsin, trypsin is preferably added to the measurement sample before or parallel with carrying out addition or the like of the fluorescent probe to the measurement sample in order to carry out the measurement based on the fluorescent probe of the invention.

A form of the body fluid sample which is a specimen for fluorescence detection is not particularly limited. However, for example, a liquid which is collected from the abdominal cavity of a patient or the like during or after a surgery; any water-absorbing materials, for example, a slip of paper such as filter paper, towels, or the like, to which an excised pancreas had been adhered; or a liquid which adheres to or flows out of the surface or the like of the pancreas itself remained in the body after excision of tumor regions; or the like can be mentioned.

As a measure which contacts the body fluid sample, which is a specimen, with the fluorescent probe, typically, addition, coating, or spraying of a solution including the fluorescent probe to the sample can be mentioned. However, the measure can properly be selected depending on a form of the above body fluid sample, measurement environments, etc.

As a measure which observes the fluorescent response, a fluorophotometer having a broad measurement wavelength can be used. However, a fluorescent imaging device which can display a fluorescence-emitting site as a two-dimensional picture can also be used. By using a fluorescent imaging measure, the fluorescence response can bidimensionally be visualized, and therefore, positions of pancreatic ducts or parts where the pancreatic fluid leakage occurs can instantly and visually be recognized. Particularly, because, during surgeries or the like, the measurement may be carried out there with respect to a body fluid sample collected from a subject, small portable fluorescence detectors and fluorescent imaging devices are preferable.

The pancreatic fluid detection method of the invention can be carried out, for example, during surgeries, during examinations, or after surgeries. In the specification, the term "surgery (surgeries)" encompasses any surgeries which are adopted for treatments of pancreatic diseases such as pancreatic cancers, bile duct cancers and the like, including scopic surgeries such as endoscopic or laparoscopic surgeries. In addition, the term "examination(s)" encompasses examinations using an endoscope and procedures such as excision or collection of tissues involved in examinations, as well as examinations or the like which is carried out against tissues separated/collected from the living body. These terms should be interpreted in the broadest meanings, and should not be interpreted to a limited extent in any meanings.

The protease measurement according to the method of the invention can generally be carried out under neutral conditions, and can be carried out, for example, within a pH range of 5.0 to 9.0, preferably within a pH range of 6.0 to 8.0, more preferably within a pH range of 6.8 to 7.6. As a measure which adjusts the pH, for example, any pH adjustors or buffers, such as phosphate buffers, well-known in the technical field can be used.

An application concentration of the fluorescent probe of the invention is not particularly limited, and, for example, a solution of a concentration of about 1 to 1,000 µM can be adopted.

As the fluorescent probe of the invention, the above-described compound represented by the general formula (I) or salt thereof may be used as it is. However, additives generally used in preparation of reagents may be combined with the compound or salt, as needed, and thus, the compound or salt may be used as a composition. As additives for using reagents in a physiological environment, for example, additives such as solubilizing agents, pH adjustors, buffers and isotonizing agents can be used, and their blending quantities can properly be selected by one skilled in the art. These compositions are generally provided as compositions in appropriate forms such as mixtures of a powder form, lyophilized products, granules, tablets, and liquids, and the compositions may be used by dissolving them in distilled water for injection or an appropriate buffer at the point of use.

(4) Kit for Pancreatic Fluid Detection

In the pancreatic fluid detection method of the invention, a kit for pancreatic fluid detection including the above-described fluorescent probe is preferably used. In particular, when the above-mentioned protease is chymotrypsin, it is preferable that the kit includes the above fluorescent probe and trypsin, and that the fluorescent probe and the trypsin are stored such that the fluorescent probe and the trypsin are not mixed during a period before the measurement is carried out. This is because, when the fluorescent probe and trypsin are mixed for a long term, they are likely to react, and therefore, it is desired that they are separately stored until just before the measurement of specimens. However, in terms of convenience, etc. of the kit, it is not always required that the fluorescent probe and trypsin are stored in separate independent containers, and integrated containers or a container having a plurality of storage regions that are linked to one another can be used as long as the containers provide environments in which the fluorescent probe and trypsin are not mixed.

The fluorescent probe of the invention or trypsin is generally prepared as a solution in the kit. However, for example, the fluorescent probe or trypsin can be provided as a composition in an appropriate form such as a mixture of a powder form, lyophilized products, granules, tablets or liquids, and the composition can be used by dissolving it in distilled water for injection or an appropriate buffer at the point of use.

In addition, the kit may also appropriately include reagents or the like other than them, as needed. As additives, for example, additives such as solubilizing agents, pH adjustors, buffers and isotonizing agents can be used, and their blending quantities can properly be selected by one skilled in the art.

EXAMPLES

Hereinafter, the invention will be described in more detail with reference to examples. However, the invention is not limited by the examples.

Example 1

According to the following scheme, gPhe-HMRG (glutamyl-phenylalanine hydroxymethyl rhodamine green), which is a fluorescent probe of the invention, was synthesized.

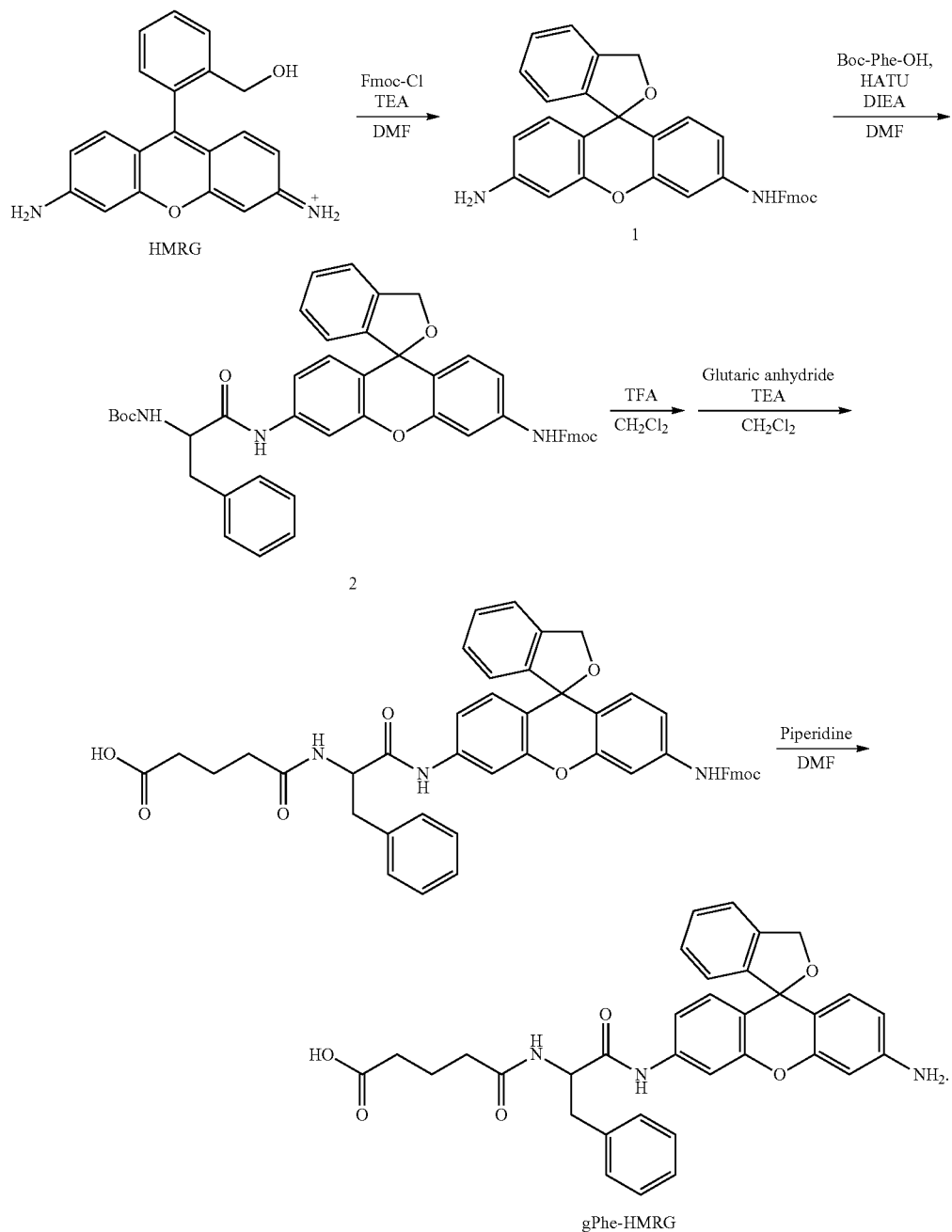

(a) Synthesis of Compound 1

55 mg of HMRG (0.174 mmol, 1 eq.) and 53.6 μL of triethylamine (0.167 mmol, 2.2 eq.) were dissolved in 2 mL of dimethylformamide (DMF), and the resulting mixture was stirred at 0° C. under an argon atmosphere for 10 minutes. Subsequently, 0.5 mL of DMF in which 67 mg of 9-fluorenylmethyl chloroformate (0.261 mmol, 1.5 eq.) had been dissolved was added thereto, and the mixture was stirred for 15 hours. The reaction solvent was removed under reduced pressure, and the residue was purified by silica gel chromatography (dichloromethane/methanol=95/5), thereby obtaining an objective compound (36 mg, 22%). In addition, see (a) of Example 2 for synthesis of HMRG.

$^1$H NMR (400 MHz, CD$_3$OD): δ 7.78 (d, 2H, J=8.1 Hz), 7.61 (d, 2H, J=7.3 Hz), 7.44-7.32 (m, 4H), 6.89-6.87 (m, 3H), 6.74-6.71 (m, 2H), 6.49-6.45 (m, 1H), 6.35 (dd, 1H, J=8.4 Hz, 1.8 Hz), 5.27 (s, 2H), 4.55 (d, 2H, J=6.6 Hz), 4.27 (t, 1H, J=6.6 Hz). HRMS (ESI$^+$) Calcd FOR [M+H]$^+$, 539.19708. Found, 539.19521 (−1.87 mmu).

(b) Synthesis of Compound 2

36 mg of Compound 1 (0.067 mmol, 1 eq.) and 30.0 μL of N,N-diisopropylethylamine (DIEA) (0.167 mmol, 2.5 eq.) were dissolved in 2 mL of DMF, and the resulting mixture was stirred at 0° C. under an argon atmosphere for 10 minutes. Subsequently, 0.5 mL of DMF in which 44.4 mg of Boc-Phe-OH(N-(tert-butoxycarbonyl)-L-phenylalanine) (0.167 mmol, 2.5 eq.) and 63.5 mg of O-(7-azabenzotriazole-1-yl)-N,N,N',N'-tetramethyluronium hexafluorophosphate (HATU) (0.167 mmol, 2.5 eq.) had been dissolved was added thereto, and the mixture was stirred for 15 hours. The reaction solvent was removed under reduced pressure, and the residue was purified by silica gel chromatography (n-hexane/ethyl acetate=66/34), thereby obtaining an objective compound (42 mg, 81%).

$^1$H NMR (400 MHz, CD$_3$OD): δ 8.01 (s, 1H), 7.77 (d, 2H, J=7.3 Hz), 7.61 (d, 2H, J=7.3 Hz), 7.41 (d, 2H, J=7.3 Hz), 7.37 (s, 1H), 7.34-7.29 (m, 5H), 7.23-7.21 (m, 5H), 7.06 (s, 1H), 6.98-6.94 (m, 2H), 6.84-6.81 (m, 3H), 5.28 (s, 2H), 4.54 (d, 2H, J=6.6 Hz), 4.51-4.48 (m, 1H), 4.26 (t, 1H, J=6.6 Hz), 3.13-3.11 (m, 2H), 1.40 (s, 9H). HRMS (ESI$^+$) Calcd FOR [M+H]$^+$, 786.31792. Found, 786.31652 (−1.41 mmu).

(c) Synthesis of gPhe-HMRG 42 mg of Compound 2 (0.053 mmol, 1 eq.) was dissolved in a 20% trifluoroacetic acid (TFA)/dichloromethane solution, and the resulting mixture was stirred at room temperature for 30 minutes. The solvent was removed under reduced pressure, and the resulting solid was extracted with a saturated aqueous solution of dichloromethane and sodium hydrogen carbonate. Sodium sulfate was added to the organic layer, followed by filtration, and then, the solvent was removed, thereby obtaining a solid. The obtained solid was dissolved in 5 mL of dichloromethane, 22.8 mg of glutaric anhydride (0.200 mmol, 3.8 eq.) and 28.2 μL of TEA (0.200 mmol, 3.8 eq.) were added thereto, and the resulting mixture was stirred at room temperature under an argon atmosphere for 15 hours. Subsequently, the solvent was removed under reduced pressure, a 20% piperidine/DMF solution was added thereto, and the mixture was stirred at room temperature for 30 minutes. The solvent was removed, and purification was carried out by using HPLC (eluent A (H$_2$O, 0.1% TFA) and eluent B (CH$_3$CN 80%, H$_2$O 20%) (A/B=80/20 to 0/100 40 min.)), thereby obtaining an objective compound (13.7 mg, 45%).

$^1$H NMR (400 MHz, CD$_3$OD): δ 8.42 (s, 1H), 7.72-7.70 (m, 2H), 7.58 (1H, t, J=6.8 Hz), 7.42-7.18 (m, 9H), 7.03 (1H, d, J=9.3 Hz), 6.95 (s, 1H), 4.75 (t, 1H, J=7.6 Hz), 4.34 (s, 2H), 3.19-3.13 (m, 1H), 3.03-3.00 (m, 1H), 2.29-2.21 (m, 4H), 1.85-1.78 (m, 2H).

$^{13}$C NMR (100 MHz, CD$_3$OD): d 176.8, 175.5, 173.4, 164.6, 161.7, 160.1, 156.9, 148.3, 141.2, 137.9, 134.8, 131.7, 130.5, 130.3, 129.8, 129.5, 129.0, 128.0, 121.5, 119.5, 119.4, 118.6, 107.1, 98.5, 63.1, 57.3, 38.9, 35.6, 33.9, 22.1 HRMS (ESI$^+$) Calcd FOR [M+H]$^+$, 578.22911. Found, 578.22659 (−2.52 mmu).

Example 2

According to the following scheme, gGlu-HMRG (γ-glutamyl hydroxymethyl rhodamine green), which is a fluorescent probe of the invention, was synthesized.

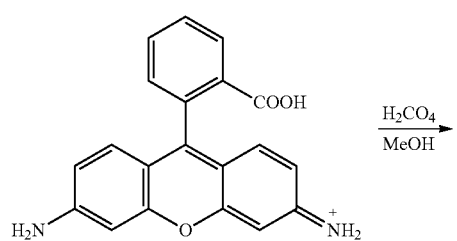

(a) Synthesis of Compound 3 (HMRG)

285 mg of rhodamine 110 (0.8 mmol, 1 eq.) was dissolved in 10 mL of methanol, followed by addition of sulfuric acid, and the resulting mixture was stirred at 80° C. under an argon atmosphere for 10 hours. The reaction solvent was removed under reduced pressure, and the residue was washed with saturated sodium bicarbonate water and water. The resulting solid was dissolved in 10 mL of tetrahydrofuran (THF), 400 μL of a 5M sodium methoxide solution (in methanol) (0.8 mmol, 1 eq.) was added thereto at 0° C. under an argon atmosphere, and the resulting mixture was stirred for 10 minutes. Subsequently, 333 mg of lithium aluminum hydride (8 mmol, 10 eq.) was added thereto, and the mixture was stirred for 3 hours. 5 mL of a saturated ammonium chloride aqueous solution was added thereto, the solvent was removed under reduced pressure, and the resulting solid was extracted with dichloromethane and a saturated aqueous solution of potassium sodium tartrate tetrahydrate. Sodium sulfate was added to the organic layer, followed by filtration, and then, the solvent was removed, thereby obtaining a solid. The obtained solid was dissolved in dichloromethane, 196 mg of chloranil (1 mmol, 1 eq.) was added thereto, and the mixture was stirred at room temperature for 30 minutes. The solvent was removed under reduced pressure, and the residue was purified by silica gel chromatography (dichloromethane/methanol=10:1), thereby obtaining an objective compound (104 mg, 41%).

$^1$H NMR (300 MHz, CD$_3$OD): δ 7.64 (d, 1H, J=7.7 Hz), 7.56 (t, 1H, J=7.6 Hz), 7.44 (t, 1H, J=7.5 Hz), 7.17 (d, 1H, J=7.5 Hz), 7.03-7.00 (m, 2H), 6.71-6.74 (m, 4H), 4.23 (s, 2H) $^{13}$C NMR (75 MHz, CD$_3$OD): δ 161.5, 159.9, 159.6, 141.0, 133.4, 132.2, 131.3, 130.3, 129.5, 128.8, 118.0, 115.0, 98.4, 62.8 HRMS (ESI$^+$) Calcd FOR [M+H]$^+$, 317.12900. Found, 317.12862 (−0.38 mmu)

(b) Synthesis of gGlu-HMRG

Compound 3 (0.05 mmol 1 eq.), HATU (0.11 mmol, 2 eq.) and N,N-diisopropylethylamine (0.11 mmol, 2 eq.) were dissolved in 2 mL of dimethylformamide (DMF), and the resulting mixture was stirred at 0° C. under an argon atmosphere for 10 minutes. Subsequently, 0.5 mL of DMF in which Boc-Glu-OtBu (0.05 mmol, 1 eq.) was dissolved was added thereto, and the mixture was stirred for 15 hours. A solid obtained after the reaction solvent was removed under reduced pressure was dissolved in 2 mL of dichloromethane and 2 mL of trifluoroacetic acid (TFA), and the mixture was stirred for 30 minutes. The solvent was removed, and purification was carried out by using HPLC (eluent A: H$_2$O, 0.1% TFA and eluent B: 80% CH$_3$CN, 20% H$_2$O, 0.1% TFA; A/B=80/20 to 0/100 FOR 40 min.), thereby obtaining an objective compound.

$^1$H NMR (400 MHz, CD$_3$OD): δ 8.39 (s, 1H), 7.62-7.61 (m, 2H), 7.50-7.47 (m, 1H), 7.39 (d, 1H, J=7.8 Hz), 7.24-7.22 (m, 3H), 6.94 (d, 1H, J=8.3 Hz), 6.86 (s, 1H), 4.25 (s, 2H), 3.96 (t, 1H, J=6.3 Hz), 2.71-2.69 (m, 2H), 2.30-2.27 (m, 2H) $^{13}$C NMR (75 MHz, CD$_3$OD): δ 173.4, 171.8, 164.5, 163.1, 160.7, 157.1, 148.7, 141.2, 134.9, 131.9, 131.7, 130.5, 129.8, 129.0, 121.4, 119.4, 118.5, 106.9, 98.5, 63.1, 53.5, 33.4, 26.6 HRMS (ESI$^+$) Calcd FOR [M+H]$^+$, 446.17160. Found, 446.17195 (+0.36 mmu).

Example 3

According to the following scheme, Bz-Tyr-HMRG (benzoyltyrosine hydroxymethyl rhodamine green), which is a fluorescent probe of the invention, was synthesized.

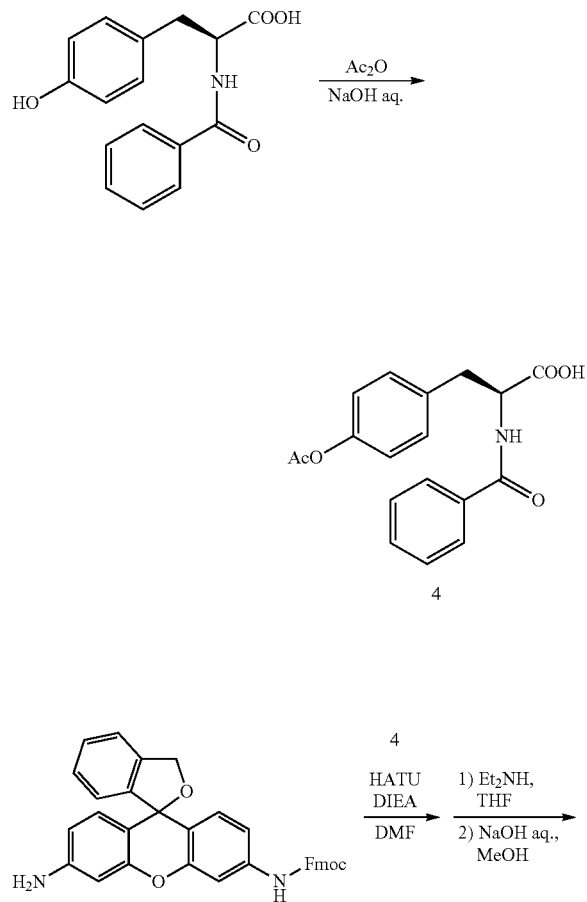

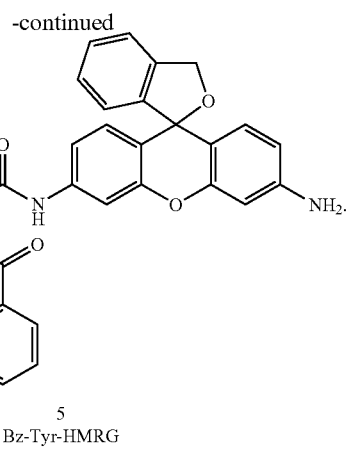

5
Bz-Tyr-HMRG (a) Synthesis of Compound 4 (Bz-Tyr(Ac)—OH, N-benzoyl-O-acetyl-tyrosine)

263 mg of sodium hydroxide (6.56 mmol) was dissolved in 1.75 mL of water. 500 mg of Bz-Tyr-OH (1.75 mmol) was added to the sodium hydroxide aqueous solution, and dissolved therein, and several pieces of ice were added thereto to thereby cool the solution to 0° C. 620 μL of acetic anhydride (6.56 mmol) was added thereto, and the mixture was stirred at 0° C. for 20 minutes. Then, 20 mL of ethyl acetate and 50 mL of water were added thereto, and the pH was adjusted to 2 with 3M hydrochloric acid. The organic layer was separated, and 20 mL of ethyl acetate was again added thereto, followed by liquid separation. Then, the organic layers were combined, and were dried with sodium sulfate. The ethyl acetate was removed under reduced pressure, and recrystallization was carried out using ethyl acetate and hexane, thereby obtaining Compound 4 (379 mg, 66%).

$^1$H NMR (400 MHz, CDCl$_3$): δ 7.68 (m, 2H), δ 7.51 (m, 1H), δ 7.41 (m, 2H), δ 7.20 (d, J=8.3, 2H), 7.02 (d, J=8.3, 2H), δ 6.66 (d, J=7.3, 1H), δ 5.08 (m, 1H), δ 3.35 (dd, J=14.2, 5.5, 1H) δ 3.27 (dd, J=14.2, 5.5, 1H), δ 2.30 (s, 3H)
$^{13}$C NMR (100 MHz, CDCl$_3$): δ 174.1, 169.9, 167.8, 149.9, 133.5, 133.4, 132.2, 130.6, 128.8. 127.2, 121.8, 53.6, 36.7, 21.2

(b) Synthesis of Compound 5 (Bz-Tyr-HMRG)

15.1 mg of Compound 4 (0.046 mmol, 5 eq.) and 17.5 mg of HATU (0.046 mmol, 5 eq.) were dissolved in 1 mL of DMF, and the resulting mixture was cooled to 0° C. under a nitrogen atmosphere. Subsequently, 9.9 μL of N,N-diisopropylethylamine (0.055 mmol, 6 eq.) was added thereto, and the mixture was stirred for 3 minutes. This was added to a solution obtained by dissolving 5 mg of Compound 1 (0.009 mmol) in 1 mL of DMF, followed by cooling the solution to 0° C. under a nitrogen atmosphere. The solution was slowly warmed to room temperature, and was stirred for 24 hours. The reaction solvent was removed under reduced pressure, 20 mL of dichloromethane was added to the residue, and the mixture was washed with 20 mL of 1M hydrochloric acid. The organic layer was dried with sodium sulfate, and then, dichloromethane was removed under reduced pressure. The residue was purified by silica gel chromatography (hexane/ethyl acetate=7/3→5/5). A fraction including an objective compound was concentrated under reduced pressure, and the residue was dissolved in 2 mL of THF. Then, 96 μL of diethylamine (0.92 mmol) was added thereto, and the mixture was stirred at room temperature for 24 hours. The reaction solvent was removed under reduced pressure, and the residue was dissolved in 2 mL of methanol.

100 μL of a 0.1 M sodium hydroxide aqueous solution was added thereto, and the mixture was stirred at room temperature for 1 hour. 100 μL of 1 M hydrochloric acid was added thereto. Then, the reaction solvent was removed under reduced pressure, and the residue was purified by HPLC (eluent A: H₂O, 0.1% TFA, and eluent B: acetonitrile, 0.1% TFA; A/B=80/20 to 0/100 for 30 min.), thereby obtaining Compound 5.

HRMS (ESI⁺) Calcd FOR [M+H]⁺, 584.21800. Found, 584.21887 (0.87 mmu).

Example 4

According to the following scheme, Glt-Ala-Ala-Phe-HMRG (Glt-AAF-HMRG: glutaryl-alanine-alanine-phenylalanine hydroxymethyl rhodamine green) and Suc-Ala-Ala-Pro-Phe-HMRG (Suc-AAPF-HMRG: succinyl-alanine-alanine-proline-phenylalanine hydroxymethyl rhodamine green), which are fluorescent probes of the invention, were synthesized.

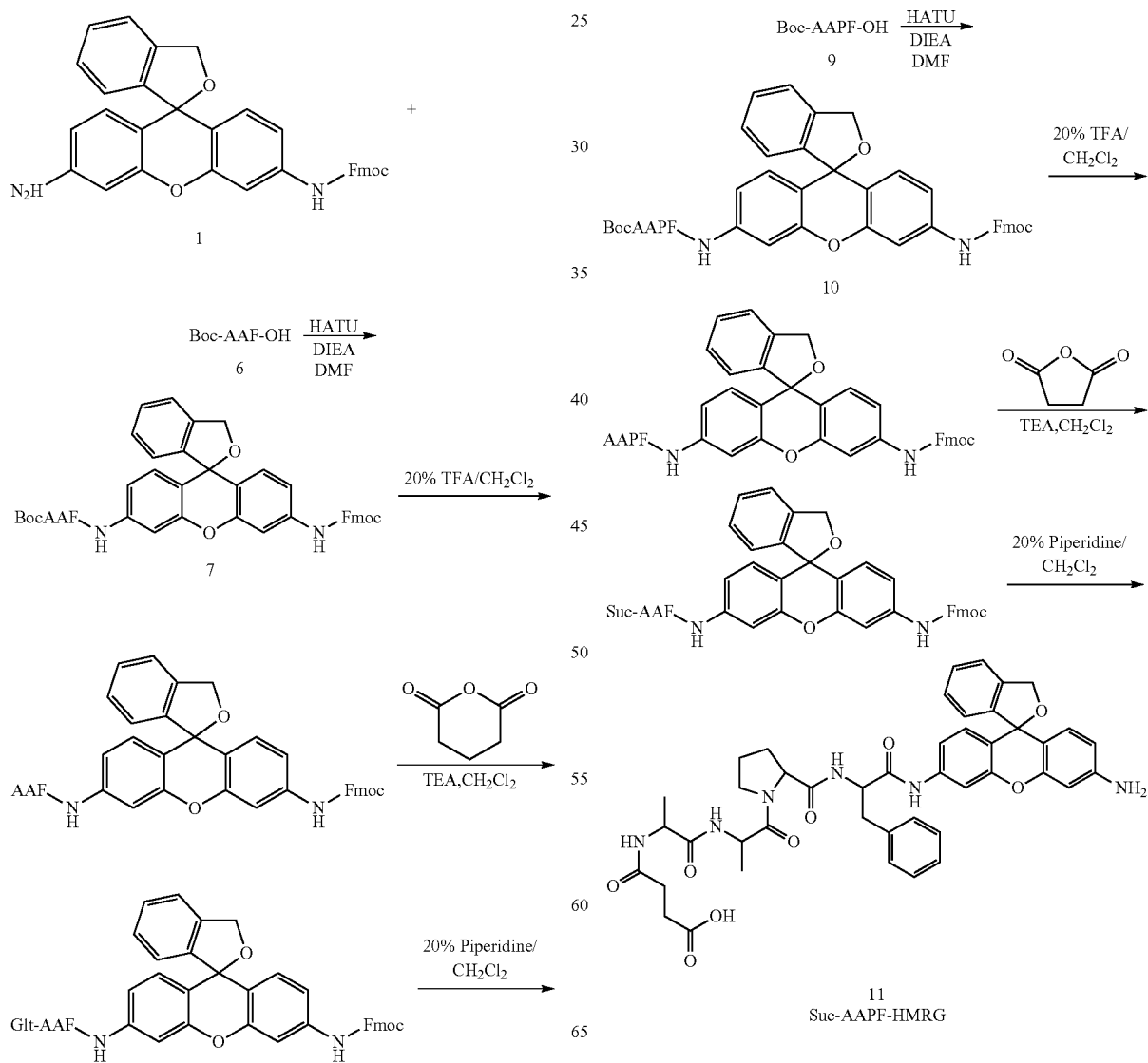

(a) Synthesis of N-Boc-Protected Peptides, Boc-AAF-OH (Compound 6) and Boc-AAPF-OH (Compound 9)

Compounds 6 and 9, which are N-Boc-protected peptides, were synthesized with Prelude automatic solid-phase synthesizer manufactured by Protein Technologies, Inc. using H-Phe-Trt(2-Cl)-Resin (0.94 mmol/g, 100-200 mesh, 1% DVB (divinylbenzene)) based on a general Fmoc solid-phase synthesis method shown below.

(1) Peptide coupling cycles: Fmoc amino acids (4 equivalents of resins) and O-(benzotriazole-1-yl)-N,N,N',N',-tetramethyluronium hexafluorophosphate (HBTU: 4 equivalents of resins) were dissolved in DMF, diisopropylethylamine (DIPEA: 8 equivalents of resins) was added thereto, and the resulting mixture was stirred. The solution was added to resins to which N-terminus-deprotected peptides had been coupled, and the mixture was stirred for 2.5 minutes.

(2) Fmoc-deprotection cycles: a 20% (v/v) piperidine/DMF solution was added to the resins, and the mixture was stirred for 12 minutes, thereby carrying out deprotection of Fmoc-protective groups.

(3) Removal from the resins: a solution of 10% acetic acid, 20% 2,2,2-trifluoroethanol and 70% dichloromethane was added to the resins, and the mixture was stirred for 1 hour, thereby removing peptides from the resins. The resins were removed by filtration, and the filtrate was removed under reduced pressure. An excessive amount of cooled diisopropylether was added to the residue, and a produced precipitate was filtered, thereby obtaining Compounds 6 and 9 which were N-Boc-protected peptides.

N-Boc-protected peptide (Compound 6) Boc-AAF-OH
ESI-MS: m/z 407[M]$^+$
N-Boc-protected peptide (Compound 9) Boc-AAPF-OH
ESI-MS: m/z 504[M]$^+$ (b) Synthesis of Compound 7

30.0 mg of Compound 6 (0.074 mmol, 4 eq.) of an N-Boc-protected peptide and 35.0 mg of HATU (0.092 mmol, 5 eq.) were dissolved in 1 mL of DMF, and the resulting mixture was cooled to 0° C. under a nitrogen atmosphere. Subsequently, 19.7 µL of N,N-diisopropylethylamine (0.11 mmol, 6 eq.) was added thereto, and the mixture was stirred for 3 minutes. This was added to a solution obtained by dissolving 10 mg of Compound 1 (0.018 mmol) in 1 mL of DMF and by then cooling the mixture to 0° C. under a nitrogen atmosphere, and the solution was slowly warmed to room temperature, and was stirred for 24 hours. The reaction solvent was removed under reduced pressure, and the residue was purified by silica gel chromatography (hexane/ethyl acetate=5/5), thereby obtaining Compound 7.

ESI-MS: m/z 928[M]$^+$ (c) Synthesis of Compound 8 (Glt-Ala-Ala-Phe-HMRG (Glt-AAF-HMRG; Glutaryl-Alanine-Alanine-Phenylalanine Hydroxymethyl Rhodamine Green))

The compound 7 obtained in (b) was dissolved in a 20% TFA/dichloromethane solution, and the resulting solution was stirred at room temperature for 30 minutes. Then, the reaction solvent was removed under reduced pressure, and 10 mL of a saturated sodium bicarbonate aqueous solution and 10 mL of dichloromethane were added thereto. The organic layer was separated, and was dried with sodium sulfate. The organic solvent was removed under reduced pressure, and 5 mL of dichloromethane, 9.7 mg of anhydrous glutaric acid (0.085 mmol, 4.7 eq.), and 11.8 µL of triethylamine (0.085 mmol, 4.7 eq.) were added thereto, and the mixture was stirred at room temperature for 20 hours. Then, the reaction solvent was removed under reduced pressure, 1 mL of a 20% piperidine/DMF solution was added thereto, and the mixture was stirred at room temperature for 1 hour. The reaction solvent was removed under reduced pressure, and the residue was purified by HPLC (eluent A: H$_2$O, 0.1% TFA and eluent B: acetonitrile, 0.1% TFA, A/B=80/20 to 0/100 FOR 30 min.), thereby obtaining a compound 8 of Glt-AAF-HMRG (3.0 mg, 23% (2 steps)).

HRMS (ESI$^+$) Calcd FOR [M+Na]$^+$, 742.28473. Found, 742.28268 (−2.05 mmu).

(d) Synthesis of Compound 10

37.3 mg of Compound 9 of an N-Boc-protected peptide (0.074 mmol, 4 eq.) and 35.0 mg of HATU (0.092 mmol, 5 eq.) were dissolved in 1 mL of DMF, and the resulting mixture was cooled to 0° C. under a nitrogen atmosphere. Subsequently, 19.7 µL of N,N-diisopropylethylamine (0.11 mmol, 6 eq.) was added thereto, and the mixture was stirred for 3 minutes. This was added to a solution obtained by dissolving 10 mg of Compound 1 (0.018 mmol) in 1 mL of DMF and by then cooling the mixture to 0° C. under a nitrogen atmosphere, and the solution was slowly warmed to room temperature, and was stirred for 24 hours. The reaction solvent was removed under reduced pressure, and the residue was purified by silica gel chromatography (hexane/ethyl acetate=7/3 to 3/7), thereby obtaining Compound 10.

ESI-MS: m/z 1025[M]$^+$ (e) Synthesis of Compound 11 (Suc-Ala-Ala-Pro-Phe-HMRG (Suc-AAPF-HMRG; Succinyl-Alanine-Alanine-Proline-Phenylalanine Hydroxymethyl Rhodamine Green))

Compound 10 obtained in (d) was dissolved in a 20% TFA/dichloromethane solution, and the mixture was stirred at room temperature for 30 minutes. Then, the reaction solvent was removed under reduced pressure, 10 mL of a saturated sodium bicarbonate aqueous solution and 10 mL of dichloromethane were added thereto. The organic layer was separated, and was dried with sodium sulfate. The organic solvent was removed under reduced pressure, 5 mL of dichloromethane, 7.8 mg of succinic anhydride (0.078 mmol, 4 eq.) and 10.9 µL of triethylamine (0.078 mmol, 4 eq.) were added thereto, and the resulting mixture was stirred at room temperature for 20 hours. Then, the reaction solvent was removed under reduced pressure, 1 mL of a 20% piperidine/DMF solution was added thereto, and the solution was stirred at room temperature for 1 hour. The reaction solvent was removed under reduced pressure, and the residue was purified by HPLC (eluent A: H$_2$O, 0.1% TFA and eluent B: acetonitrile, 0.1% TFA, A/B=80/20 to 0/100 FOR 30 min.), thereby obtaining Compound 8 of Suc-AAPF-HMRG (4.1 mg, 28% (2 steps)).

HRMS (ESI$^+$) Calcd FOR [M+Na]$^+$, 825.32185. Found, 825.32122 (−0.63 mmu).

Example 5

Fluorescence Assay Using Chymotrypsin

The gPhe-HMRG compound having an amino acid residue based on N-substituted phenylalanine synthesized in Example 1 was dissolved in a neutral phosphate buffer, and chymotrypsin was allowed to act thereon, thereby carrying out the fluorescence assay. 3 µL of a 2.4 mM gPhe-HMRC dimethylsulfoxide (DMSO) solution was dissolved in 3 mL of 0.1 M sodium phosphate buffer (pH 7.4) at a final concentration of 2.4 µM, 4.6 U of chymotrypsin (a-chymotrypsin derived from bovine pancreas: SIGMA C4129-250MG) was added thereto to conduct an enzymatic reaction at 37° C. The excitation wavelength was set to 501 nm. The obtained results are shown in FIGS. 1 and 2.

Figure 2:
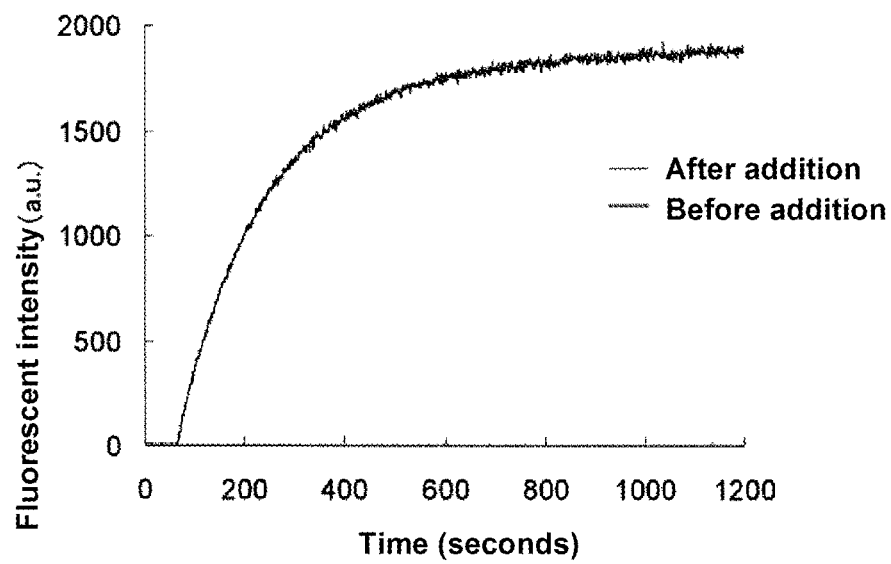
FIG. 2 is a diagram showing time-course changes in the fluorescent intensity by chymotrypsin addition to gPhe-HMRG which is a fluorescent probe of the invention. The arrow in the figure shows the time point of chymotrypsin addition.

As a result of the fluorescence assay, it was recognized that addition of chymotrypsin caused significant increases in the absorption and the fluorescent intensity (FIG. 1). As to the response speed, a rapid increase in the fluorescent intensity was observed immediately after addition of chymotrypsin at 524 nm, which is a peak wavelength of the fluorescence, and it was recognized that the fluorescent intensity reached saturation after about 600 seconds (FIG. 2). The results show that the amide bond in gPhe-HMRG is hydrolyzed by an enzymatic reaction of chymotrypsin with gPhe-HMRG, thus producing a ring-opened product, i.e. that gPhe-HMRG functions as an on/off fluorescent probe against chymotrypsin. In addition, in changes in the absorption spectrum of FIG. 1, a significant change in the absorbance was observed around 500 nm, and therefore, it can be understood that, by observing changes in the absorbance in the wavelength region, the reaction of chymotrypsin and gPhe-HMRG can be recognized.

Example 6

Figure 3:
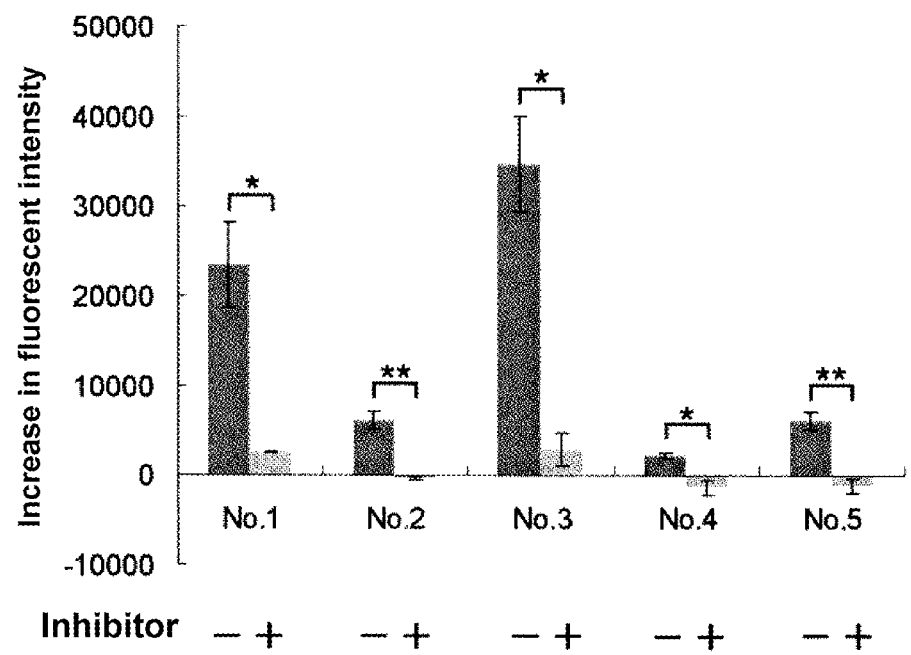
FIG. 3 is a diagram showing changes in the fluorescent intensity by addition of a pancreatic fluid sample to gGlu-HMRG which is a fluorescent probe of the invention, and γ-glutamyltransferase specificity of the responses. In the figure, cases where an inhibitor was added are indicated as "+", while cases where the inhibitor was not added are indicated as "−". Values of the bar graph were calculated as standard errors with a sample number of 3 (* indicates $p<0.05$, and ** indicates $p<0.01$).

In Vitro Fluorescence Assay (gPhe-HMRG, gGlu-HMRG) Using Human Pancreatic Fluid gPhe-HMRG synthesized in Example 1 and gGlu-HMRG, which has a glutamic acid residue, synthesized in Example 2 were used as fluorescent probes to evaluate enzymatic activities of pancreatic fluid obtained from patients of pancreatic cancer or bile duct cancer. 1 µL of a fluorescent probe DMSO solution (1 mM) was dissolved in 180 µL of a 0.1 M sodium phosphate buffer (pH 7.4) at a final concentration of 0.9 µM, 20 µL of a pancreatic fluid was added thereto, and an enzymatic reaction was carried out at 37° C. for 30 minutes. In the case of gPhe-HMRG, a probe solution to which 57 BAEE units of trypsin (bovine pancreas-derived trypsin: SIGMA T1426-100MG) had been added was used to carry out the same enzymatic reaction. In addition, as to inhibitor treatments for comparisons, 1 µL of an aqueous solution (10 mM) of a γ-glutamyltransferase inhibitor (GGs-Top: Wako Pure Chemical 075-05471) in the case of gGlu-HMRG, and 1 µL of a DMSO solution (10 mM) of a chymotrypsin inhibitor (chymostatin: SIGMA C7268) in the case of gPhe-HMRG were each added to probe solutions. For excitation wavelengths and fluorescence wavelengths of a fluorescence measurement device, 478-492 nm and 523-548 nm, respectively, were used. The results obtained with respect to gGlu-HMRG and gPhe-HMRG are shown in FIGS. 3 and 4, respectively.

As a result of the assay based on gGlu-HMRG, increases in fluorescent intensities were observed in all pancreatic fluid samples (No. 1 to No. 5). In addition, when the γ-glutamyltransferase-specific inhibitor was added thereto, the fluorescent intensity significantly decreased. Thus, it was confirmed that gGlu-HMRG could specifically detect a γ-glutamyltransferase activity in a pancreatic fluid.

Figure 4:
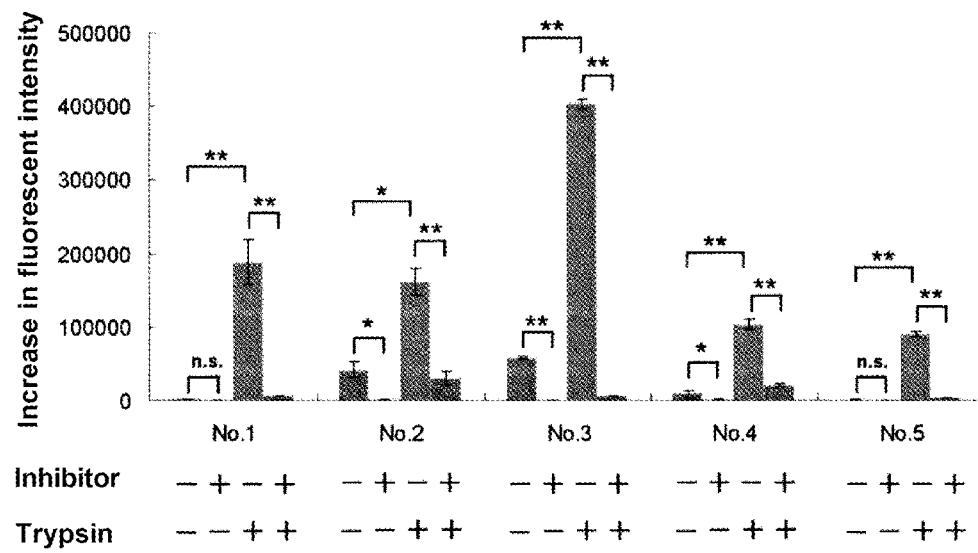
FIG. 4 is a diagram showing changes in the fluorescent intensity by addition of a pancreatic fluid sample to gPhe-HMRG which is a fluorescent probe of the invention, and chymotrypsin specificity of the responses. In the figure, cases where an inhibitor and trypsin were each added are indicated as "+", while cases where the inhibitor and trypsin were not added are indicated as "−". Values of the bar graph were calculated as standard errors with a sample number of 3 (* indicates $p<0.05$, and ** indicates $p<0.01$).

In the case of the assay based on gPhe-HMRG, because target chymotrypsin is present as a precursor (chymotrypsinogen) in pancreatic fluid, influences of the presence or absence of addition of trypsin which activates the body were measured together, besides influences of the presence or absence of the chymotrypsin inhibitor (FIG. 4). As a result, when trypsin was included in solutions, remarkable increases in fluorescent intensities were observed in all the pancreatic fluid samples (No. 1 to No. 5). That is, although gPhe-HMRG hardly showed a fluorescence response against chymotrypsinogen, which is a precursor, gPhe-HMRG showed an excellent fluorescence response against chymotrypsin after activation with trypsin. In addition, when chymostatin, which is an inhibitor for chymotrypsin, was added, the fluorescent intensity significantly decreased. From the results, it was confirmed that gPhe-HMRG could specifically detect chymotrypsin activities in pancreatic fluid.

Furthermore, response behaviors of the fluorescent probes against body fluids other than pancreatic fluid were compared by using drain samples which were collected from patients who received resectional surgeries of the pancreas. With respect to a total of 76 samples of pancreatic fluid, ascitic fluids and intestinal fluids which were collected from 18 patients, changes in fluorescent intensities were measured for gGlu-HMRG, gPhe-HMRG, and trypsin-added gPhe-HMRG (gPhe-HMRG-Try).

180 µL of a probe solution (1.1 µM) was poured into each well of a 96-well microplate reader (SH-8000, Hitachi), and then, 20 µL of a collected sample was added thereto, followed by mixing them. The sample was incubated at 37° C., and fluorescence responses were measured after 5 minutes, 15 minutes and 30 minutes. Trypsin was added to gPhe-HMRG-Try at a final concentration of 0.525 µBTEE/µL. For an excitation wavelength and a fluorescence wavelength for the fluorescence measurement device, 490 nm and 520 nm, respectively, were used. The obtained results of fluorescence responses are shown as average values of respective samples in FIG. 5.

Figure 5:
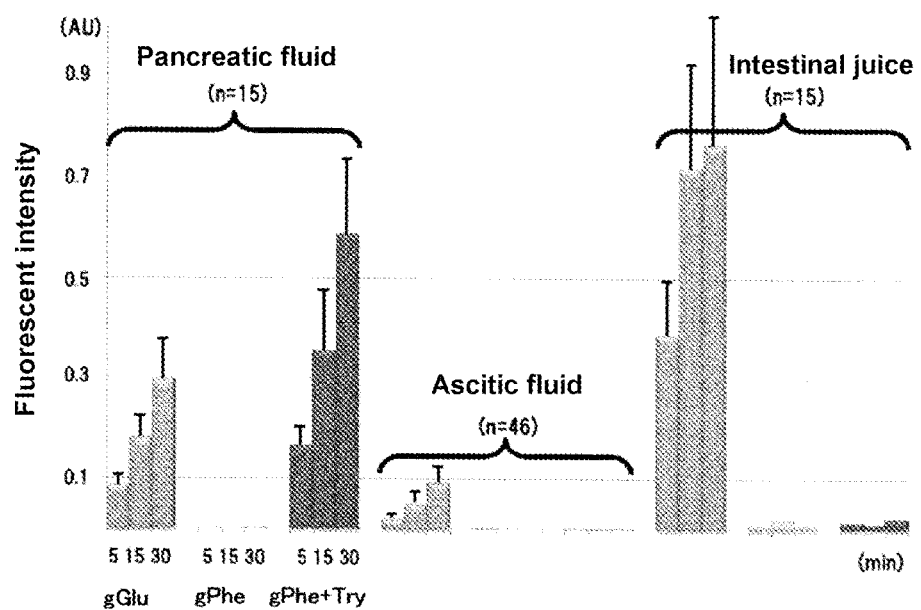
FIG. 5 is a diagram showing a time-course changes in fluorescent intensities of gGlu-HMRG, gPhe-HMRG and trypsin-added gPhe-HMRG (gPhe-HMRG-Try) with respect to pancreatic fluid, ascitic fluids and intestinal fluid which had been collected from patients.

From FIG. 5, while significant fluorescent responses were not observed for all the body fluids in the case of gPhe-HMRG alone where trypsin was not added, large increases in fluorescent intensities were observed only for pancreatic fluids in gPhe-HMRG-Try where trypsin was added. This shows that gPhe-HMRG specifically reacts with chymotrypsin, which is activated by addition of trypsin, in pancreatic fluids. On the other hand, although an increase in fluorescent intensities was observed for pancreatic fluids in gGlu-HMRG, increases in fluorescent intensities were observed also for ascitic fluids and intestinal fluids, and, in particular, a larger increase in fluorescent intensities was observed for intestinal fluids, than for the case of pancreatic fluids. For this, it is considered that the probe responded to γ-glutamyltransferase included in intestinal fluids. From the results, it was proved that it is very useful to use a chymotrypsin activity as an index for distinguishing and identifying other body fluids and pancreatic fluids, and that combination of gPhe-HMRG and trypsin makes it possible to selectively detect pancreatic fluids.

In addition, gPhe-HMRG (trypsin added) showed a fluorescence response superior to gGlu-HMRG as described above. However, it is considered that gGlu-HMRG is very beneficial in case of an environment where intestinal fluids or the like do not exist, from a viewpoint that the fluorescent probe molecule alone (i.e., without requiring trypsin addition) can detect pancreatic fluids.

Example 7

In Vitro Fluorescence Assay

Compounds 5, 8 and 11

In the same manner as above-described Examples 6, by using, as fluorescent probes, Bz-Tyr-HMRG (Compound 5) synthesized in Example 3, as well as Glt-AAF-HMRG (Compound 8) and Suc-AAPF-HMRG (Compound 11) synthesized in Example 4, their reactivities against chymotrypsin were evaluated. The measurement conditions are as follows.

<Measurement Conditions>

Substrate final concentration: 1 μM (a stock concentration was calculated based on an absorbance at pH 3, and the final concentration was adjusted.)

Figure 6:
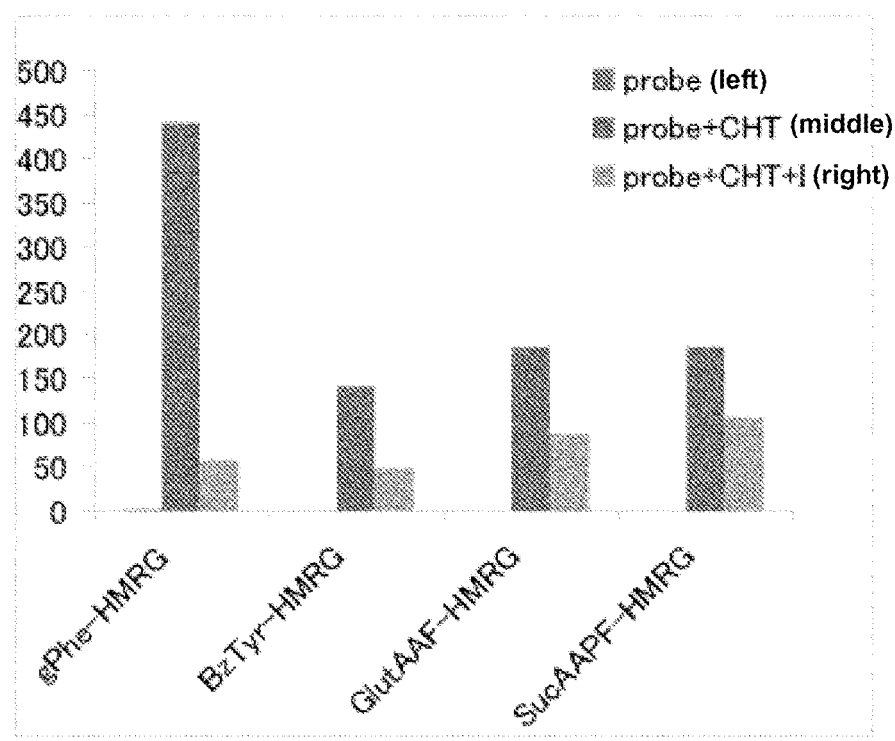
FIG. 6 is a diagram showing changes in fluorescent intensities by chymotrypsin addition to Bz-Tyr-HMRG, Glt-AAF-HMRG and Suc-AAPF-HMRG which are fluorescent probes of the invention, and chymotrypsin specificity of the responses.

Buffer solution: PBS, pH 7.4
Inhibitor (chymostatin): 10 μM
Chymotrypsin: 2 U
Incubation time: 10 minutes, 20 minutes, 30 minutes (FIG. 6 shows values of fluorescent intensities after 30 minutes).
Measurement device: Corona plate reader (SH8000)
Excitation fluorescence wavelength: 501 nm, 524 nm The obtained results of fluorescence responses are each shown as average values of plural samples in FIG. 6. As a result, increases in fluorescent intensities were observed for all fluorescent probes. In addition, the fluorescent intensity significantly decreased when the chymotrypsin inhibitor (chymostatin) was added. Thus, it was proved that all of the fluorescent probes could specifically detect chymotrypsin activities in pancreatic fluids.

Example 8

Fluorescent Imaging of Human Pancreatic Fluid

Figure 7:
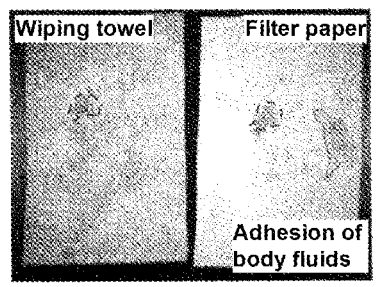
FIG. 7 is a diagram showing fluorescent imaging pictures of pancreatic fluid using gPhe-HMRG which is a fluorescent probe of the invention.
Figure 7:
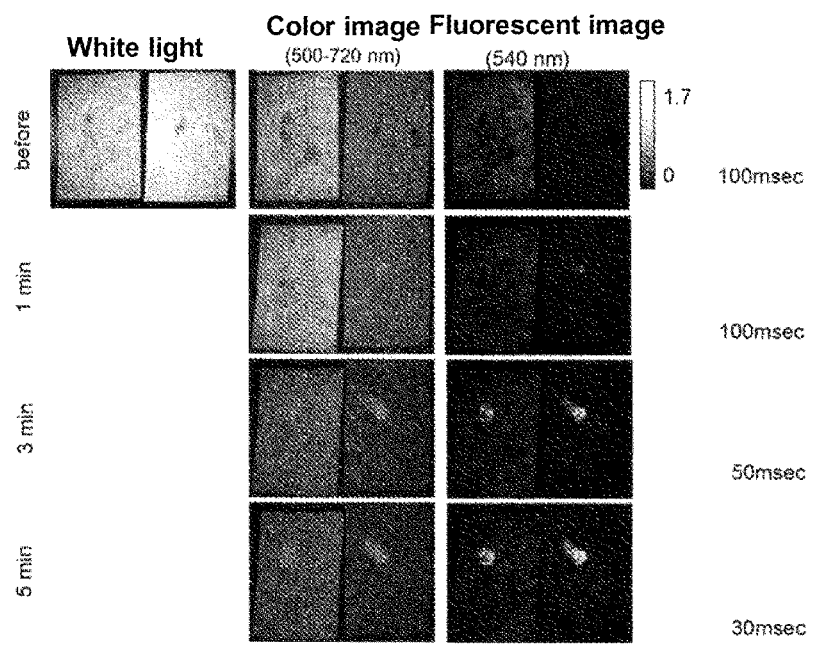
Figure 8:
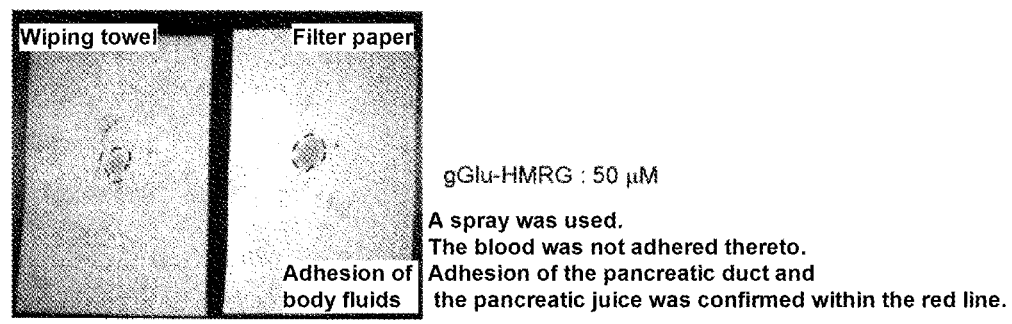
FIG. 8 is a diagram showing fluorescent imaging pictures of pancreatic fluid using gGlu-HMRG which is a fluorescent probe of the invention.
Figure 8:
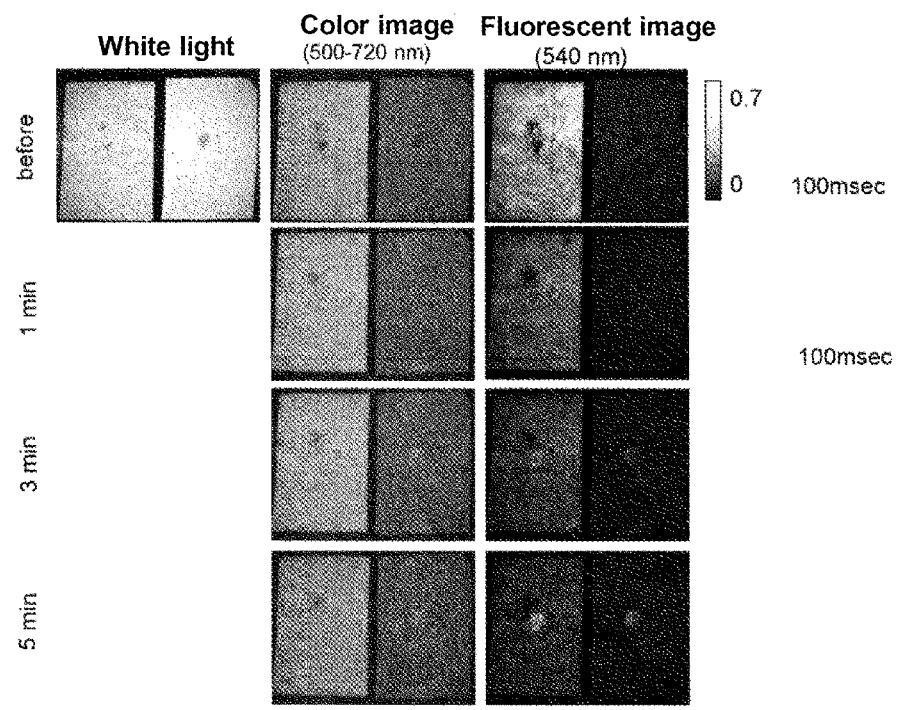

Fluorescent imaging of pancreatic fluids on an excised surface of the pancreas was carried out by using gPhe-HMRG and gGlu-HMRG as fluorescent probes. In consideration of, for example, cases where materials retaining pancreatic fluids, which are measurement subjects, are used during surgeries, wiping towels and filter paper for experiments (those having low background fluorescence from paper itself), which had been used in clinical practice, were used as the materials. For specific procedures, apiece of the pancreas immediately after being excised by surgical operations was collected, the wiping towel and filter paper was adhered to its excised surface, thereby adhering the pancreatic fluid thereto. Then, probe solutions of gPhe-HMRG (including trypsin) and gGlu-HMRG were sprayed to the adhered paper to start imaging. For the probe solutions, 10 μL of a DMSO solution (10 mM) of each probe was dissolved in 2 mL of RPMI 1640 medium (GINBO 11835) at a final concentration of 50 μM, and, for gPhe-HMRG, a solution obtained by adding trypsin (52.6 BTEE units) thereto was used. For an excitation filter and a fluorescence filter, long path filters of 435-480 nm and 490 nm, respectively, were used. The obtained image pictures are shown in FIGS. 7 and 8.

FIGS. 7a and 8a show adhesion points of the pancreatic fluid as white-light images. The left sides of FIGS. 7b and 8b are color images at 500-720 nm, and the right sides thereof show fluorescent images at 540 nm. As a result, visualization of adhesion points of the pancreatic fluids was successfully accomplished in a both gPhe-HMRG and gGlu-HMRG after several minutes from spraying of the probes. In particular, in gPhe-HMRG, clear fluorescence responses which could be distinguished by the naked eye were recognized after one minute from spraying. In addition, any fluorescence response was not observed with respect to adhesion points of body fluids other than the pancreatic fluid (within the box of the blue solid line in FIG. 7a) in gPhe-HMRG. Therefore, it was proved that selective detection of the presence of the pancreatic fluid and imaging thereof were possible by confirming the fluorescence response.

The invention claimed is:

1. A fluorescent probe for pancreatic fluid detection, comprising a compound represented by the following formula (I) or a salt thereof:

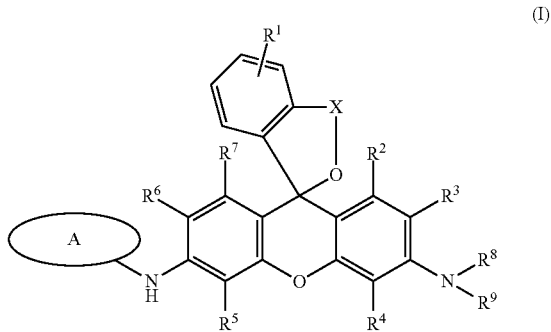

wherein A represents an amino add residue or an N-substituted amino acid residue, where A links to the adjacent NH in the formula by forming an amide bond;
$R^1$ represents a hydrogen atom, or one substituent group or two to four substituent groups which are identical to or different from each other binding to the benzene ring;
$R^2$, $R^3$, $R^4$, $R^5$, $R^6$, and $R^7$ each independently represents a hydrogen atom, a hydroxy group, an alkyl group, or a halogen atom;
$R^8$ and $R^9$ each independently represents a hydrogen atom or an alkyl group; and
X represents a $C_1$-$C_3$ alkylene group.

2. The fluorescent probe according to claim 1, wherein the amino acid is selected from aromatic amino acids.

3. The fluorescent probe according to claim 1, wherein A is as group represented by the following formula (II);

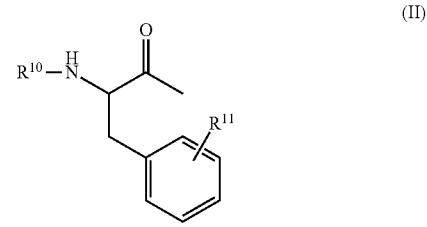

wherein $R^{10}$ represents a substituted or unsubstituted acyl group, and $R^{11}$ represents a hydrogen atom or a hydroxy group.

4. The fluorescent probe according to claim 3, wherein $R^{10}$ is selected limn an acetyl group; a carbobenzoxy group; a benzoyl group; a succinyl group; a glutaryl group; an amino acid residue whose N-terminus is substituted with an acetyl group; a carbobenzoxy group, a benzoyl group, a succinyl group or a glutaryl group; or a peptide group containing 1 to 5 amino acids whose N-terminal amino group is substituted with an acetyl group, a carbobenzoxy group, a benzoyl group, a succinyl group or a glutaryl group; or a substituent group containing any of them as one part.

5. The fluorescent probe according, to claim 1, wherein A is selected from groups represented by the following formulas (III) to (VI)

(III)
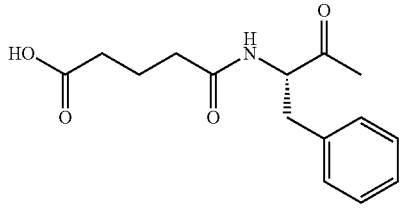

(IV)
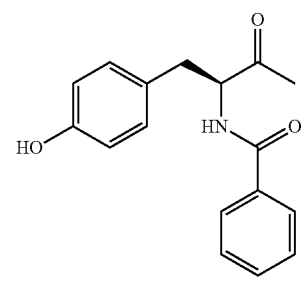

(V)
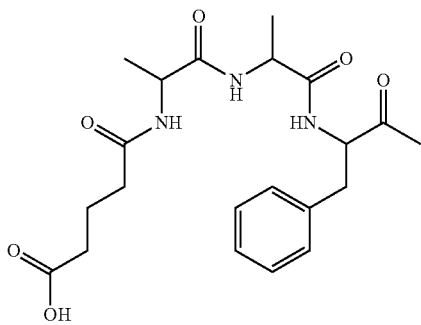

(VI)
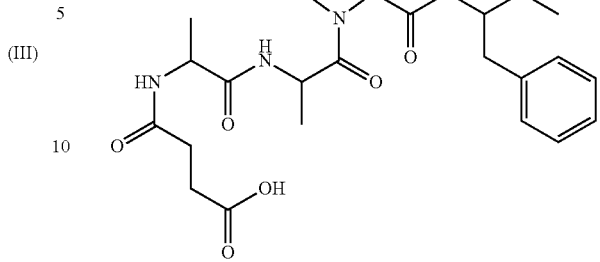

6. The fluorescent probe according to claim 1, wherein $R^1$, $R^2$, $R^3$, $R^4$, $R^5$, $R^6$, $R^7$, $R^8$, and $R^9$ are hydrogen atoms, and X is a methylene group.

7. The fluorescent probe according to claim 1, wherein A is a γ-glutamyl group.

8. The fluorescent probe according to claim 7, wherein $R^1$, $R^2$, $R^3$, $R^4$, $R^5$, $R^6$, $R^7$, $R^8$, and $R^9$ are hydrogen atoms, and X is a methylene group.

9. A method for detecting pancreatic fluid, comprising;
contacting the fluorescent probe according to claim 1 with a body fluid sample; and
observing a fluorescence response or absorbance change caused by a reaction of a protease included in the sample and the fluorescent probe to thereby detect a presence of a pancreatic fluid.

10. The method according to claim 9, wherein the protease is chymotrypsin.

11. The method according to claim 10, comprising: adding trypsin to the body fluid sample in contacting the fluorescent probe with the body fluid sample.

12. The method according to claim 9, wherein the protease is γ-glutamyltransferase.

13. The method according to claim 9, further comprising: visualizing the fluorescence response with a fluorescent imaging measure.

14. A kit for pancreatic fluid detection, comprising: the fluorescent probe according to claim 1.

15. A kit for pancreatic fluid detection, comprising: the fluorescent probe according to claim 1; and trypsin, wherein the fluorescent probe and the trypsin are stored such that the fluorescent probe and the trypsin are not mixed during a period before the kit is used.

* * * * *

UNITED STATES PATENT AND TRADEMARK OFFICE
CERTIFICATE OF CORRECTION

PATENT NO. : 9,506,102 B2  
APPLICATION NO. : 14/398202  
DATED : November 29, 2016  
INVENTOR(S) : Yasuteru Urano Page 1 of 1

It is certified that error appears in the above-identified patent and that said Letters Patent is hereby corrected as shown below:

Column 28, Line 26 (Claim 1, Line 4) please change "amino add" to --amino acid--

Signed and Sealed this  
Fourth Day of April, 2017

Michelle K. Lee  
*Director of the United States Patent and Trademark Office*